(12) United States Patent
Bartsch et al.

(10) Patent No.: US 8,835,418 B2
(45) Date of Patent: Sep. 16, 2014

(54) HEXAFLUOROISOPROPYL CARBAMATE DERIVATIVES, THEIR PREPARATION AND THEIR THERAPEUTIC APPLICATION

(71) Applicant: SANOFI, Paris (FR)

(72) Inventors: Regine Bartsch, Paris (FR); Dorothee Cheuret, Paris (FR); Luc Even, Paris (FR); Christian Hoornaert, Paris (FR); Jean Jeunesse, Paris (FR); Frank Marguet, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/688,922

(22) Filed: Nov. 29, 2012

(65) Prior Publication Data
US 2013/0165422 A1  Jun. 27, 2013

Related U.S. Application Data

(63) Continuation of application No. PCT/IB2011/052458, filed on Jun. 6, 2011.

(30) Foreign Application Priority Data

Jun. 4, 2010  (FR) ....................................... 10 54411

(51) Int. Cl.
| | | |
|---|---|---|
| A61K 31/00 | (2006.01) | |
| A01N 43/00 | (2006.01) | |
| C07D 295/20 | (2006.01) | |
| C07D 211/34 | (2006.01) | |
| C07D 211/54 | (2006.01) | |
| C07D 211/22 | (2006.01) | |
| C07D 211/46 | (2006.01) | |
| C07D 405/12 | (2006.01) | |
| C07D 413/04 | (2006.01) | |
| C07D 211/16 | (2006.01) | |
| C07D 413/06 | (2006.01) | |
| C07D 211/18 | (2006.01) | |
| C07D 211/32 | (2006.01) | |
| C07D 207/14 | (2006.01) | |
| C07D 401/12 | (2006.01) | |
| C07D 211/62 | (2006.01) | |
| C07D 211/58 | (2006.01) | |
| C07D 417/12 | (2006.01) | |
| C07D 413/12 | (2006.01) | |
| C07D 205/04 | (2006.01) | |
| C07D 285/14 | (2006.01) | |
| C07D 409/12 | (2006.01) | |
| C07D 207/12 | (2006.01) | |
| C07D 249/18 | (2006.01) | |
| C07D 401/04 | (2006.01) | |
| C07D 207/16 | (2006.01) | |
| C07D 403/04 | (2006.01) | |
| C07D 239/42 | (2006.01) | |

(52) U.S. Cl.
CPC ............ *C07D 205/04* (2013.01); *C07D 295/20* (2013.01); *C07D 211/34* (2013.01); *C07D 211/54* (2013.01); *C07D 211/22* (2013.01); *C07D 211/46* (2013.01); *C07D 405/12* (2013.01); *C07D 413/04* (2013.01); *C07D 211/16* (2013.01); *C07D 413/06* (2013.01); *C07D 211/18* (2013.01); *C07D 211/32* (2013.01); *C07D 207/14* (2013.01); *C07D 401/12* (2013.01); *C07D 211/62* (2013.01); *C07D 211/58* (2013.01); *C07D 417/12* (2013.01); *C07D 413/12* (2013.01); *C07D 285/14* (2013.01); *C07D 409/12* (2013.01); *C07D 207/12* (2013.01); *C07D 249/18* (2013.01); *C07D 401/04* (2013.01); *C07D 207/16* (2013.01); *C07D 403/04* (2013.01); *C07D 239/42* (2013.01)
USPC ............... 514/210.18; 514/230.5; 514/210.17

(58) Field of Classification Search
None
See application file for complete search history.

(56) References Cited

U.S. PATENT DOCUMENTS

| | | | | |
|---|---|---|---|---|
| 2009/0286812 A1* | 11/2009 | Erickson et al. | ........... | 514/262.1 |
| 2012/0015950 A1 | 1/2012 | Abouabdellah et al. | | |

FOREIGN PATENT DOCUMENTS

| | | |
|---|---|---|
| WO | WO95/17439 | 6/1995 |
| WO | WO98/55450 | 12/1998 |
| WO | WO2007/073168 | 6/2007 |
| WO | WO2008/106047 | 9/2008 |
| WO | WO 2009/052319 | 4/2009 |
| WO | WO 2009/141238 | 11/2009 |
| WO | WO 2010/009207 | 1/2010 |
| WO | WO2010/055267 | 5/2010 |

OTHER PUBLICATIONS

International Search Report for WO2011/151808 dated Dec. 8, 2011.

(Continued)

*Primary Examiner* — Dennis Heyer
*Assistant Examiner* — Daniel M Podgorski
(74) *Attorney, Agent, or Firm* — Kelly L. Bender

(57) ABSTRACT

The disclosure relates to hexafluoroisopropyl carbamate derivatives of general formula (I):

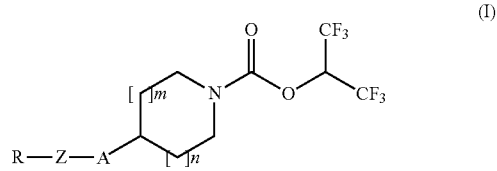

in which:
R, Z, A, m, and n are as defined in the disclosure;
in the form of the base or of an addition salt with an acid, and to the preparation process and therapeutic application thereof.

27 Claims, No Drawings

(56) References Cited

OTHER PUBLICATIONS

Long, et al., Characterization of Tunable Piperidine and Piperazine Carbamates as Inhibitors of Endocannabinoid Hydrolases, J. Med. Chem., (2010), vol. 53, pp. 1830-1842.
Konakahara, et al., A Convenient Method for the Synthesis of Activated N-Methylcarbamates, Synthesis, (1993), pp. 103-106, vol. 1.
Tsunokawa, et al., A Versatile Method for Preparation of O-Alkylperoxycarbonic Acids: Epoxidation With Alkyloxycarbonylimidazoles and Hydrogen Peroxide, Tetrahedron Letters, vol. 23, No. 20, pp. 2113-2116, (1982).
Kondo, et al., 2-Arachidonoylglycerol, an Endogenous Cannabinoid Receptor Agonist: Identification as One of the Major Species of Monoacylglycerols in Various Rat Tissues, and Evidence for its Generation Through Ca2+-Dependent and -independent Mechanisms, FEBS Letters, vol. 429, (1998), pp. 152-156.
Karlsson, et al., CDNA Cloning, Tissue Distribution, and Identification of the Catalytic Triad of Monoglyceride Lipase, The Journal of Biological Chemistry, vol. 272, No. 43, (1997), pp. 27218-27223.
Dinh, et al., Brain Monoglyceride Lipase Participating in Endocannabinoid Inactivation, PNAS, vol. 99, No. 16, pp. 10819-10824, (2002).
Saario, et al., Monoglyceride Lipse-Like Enzymatic Activity is Responsible for Hydrolysis of 2-Arachidonoylglycerol in Rat Cerebellar Membranes, Biochemical Pharmacology, vol. 67, (2004), pp. 1381-1387.
Dinh, et al., RNA Interference Suggests a Primary Role for Monoacylglycerol Lipase in the Degradation of the Endocannabinoid 2-Arachidonoylglycerol, Molecular Pharmacology, vol. 66, No. 6, pp. 1260-1264, (2004).
Sugiura, et al., Evidence That the Cannabinoid CB1 Receptor is a 2-Arachidonoylglycerol Receptor, The Journal of Biological Chemistry, vol. 274, No. 5, pp. 2794-2801, (1999).
Sugiura, et al., Evidence That 2-Arachidonoylglycerol but Not N-Palmitoyiethanolamine or Anandamide is the Physiological Ligand for the Cannabinoid CB2 Receptor, The Journal of Biological Chemistry, vol. 275, No. 1, (2000), pp. 605-612.
Savinainen, et al., Despite Substantial Degradation, 2-Arachidonoylglycerol is a Potent Full Efficacy Agonist Mediating CB1 Receptor-Dependent G-Protein Activation in Rat Cerebellar Membranes, British Journal of Pharmacology, (2001), vol. 134, pp. 664-672.
Sugiura, et al., Biochemistry, Pharmacology and Physiology of 2-Arachidonoylglycerol, an Endogenous Cannabinoid Receptor Ligand, Progress in Lipid Research, vol. 45, (2006), pp. 405-446.
Marzo, Targeting the Endocannabinoid System: to Enhance or Reduce?, Nature Reviews, Drug Discovery, vol. 7, (2008), pp. 438-455.
Tsunokawa, et al., A New Oxgenating Method Using 1-Alkoxycarbony1-1,2,4-Triazoles and Hydrogen Peroxide Relative Reactivity of O-Alkylperoxycarbonic Acids, Chem. Pharm. Bull., vol. 31, No. 12, pp. 4578-4581, (1983).

\* cited by examiner

HEXAFLUOROISOPROPYL CARBAMATE DERIVATIVES, THEIR PREPARATION AND THEIR THERAPEUTIC APPLICATION

This application is a continuation of International Application No. PCT/IB2011/052458, filed Jun. 6, 2011, which is incorporated herein by reference, and which claims the benefit of priority of French Application No. 1054411, filed Jun. 4, 2010.

The present invention relates to hexafluoroisopropyl carbamate derivatives, to their preparation and to their therapeutic application. These compounds have an inhibitory activity with regard to the enzyme MGL (monoacyl glycerol lipase).

WO 2009141238 and WO 2010009207 disclose GPR119 receptor agonists which can comprise a hexafluoroisopropyl carbamate.

"Characterization of the Tunable Piperidine and piperazine Carbamates as Inhibitors of Endocannabinoid Hydrolases" (J. Z. Long, X Jin, A. Adibekian, W. Li et al.) describes inhibitors of the enzyme MGL exhibiting an N-piperidine ring carrying a carbamate.

WO 2009/052319 discloses other types of compounds which are inhibitors of the enzyme MGL.

A subject-matter of the invention is the compounds of formula (I):

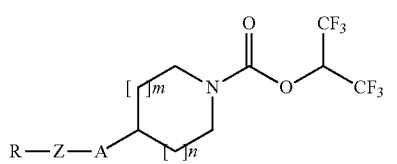

in which:

R represents an $R^1$ group optionally substituted by one or more $R^2$ and/or $R^3$ groups;

$R^1$ represents an aryl or heteroaryl group;

$R^2$ represents a halogen atom or a cyano, nitro, oxo, $(C_1\text{-}C_6)$alkyl, $(C_1\text{-}C_6)$alkoxy, hydroxyl, $(C_1\text{-}C_6)$alkylthio, $(C_1\text{-}C_6)$haloalkyl, $(C_1\text{-}C_6)$haloalkoxy, $(C_1\text{-}C_6)$haloalkylthio, $NR^4R^5$, $NR^4COR^5$, $NR^4SO_2R^5$, $COR^4$, $CO_2R^4$, $CONR^4R^5$, $SO_2R^4$, $SO_2NR^4R^5$, phenyloxy or benzyloxy group;

$R^3$ represents a monocyclic aryl or heteroaryl group which can be substituted by one or more $R^2$ groups which are identical to or different from one another;

$R^4$ and $R^5$ represent, independently of one another, a hydrogen atom or a $(C_1\text{-}C_6)$alkyl group or form, with the nitrogen atom or the N—CO or N—SO$_2$ fragment which carries them, a heterocycle optionally substituted by a $(C_1\text{-}C_6)$alkyl or benzyl group;

Z represents a bond, a $(C_1\text{-}C_6)$alkylene group, a $(C_2\text{-}C_6)$alkenylene group, a $(C_2\text{-}C_6)$alkynylene group, an O—$(C_1\text{-}C_6)$alkylene group or an $N(R^A)$—$(C_1\text{-}C_6)$alkylene group;

A represents a bond, an oxygen atom, a sulphur atom, an $N(R^A)$ group, an $N(R^A)$—$(C_1\text{-}C_6)$alkylene group, a $CON(R^A)$ group, a $CON(R^A)$—$(C_1\text{-}C_6)$alkylene group, an $SO_2N(R^A)$ group, an $SO_2N(R^A)$—$(C_1\text{-}C_6)$alkylene group, an OCON($R^A$) group, an OCON($R^A$)—$(C_1\text{-}C_6)$alkylene group, an N($R^B$)CON($R^A$) group, an N($R^B$)CON($R^A$)—$(C_1\text{-}C_6)$alkylene group, an N($R^B$)SO$_2$N($R^A$) group, an N($R^B$)SO$_2$N($R^A$)—$(C_1\text{-}C_6)$alkylene group, an O—$(C_1\text{-}C_6)$alkylene group, an N($R^B$)CO$_2$ group, an N($R^B$)CO$_2$—$(C_1\text{-}C_6)$alkylene group, an S—$(C_1\text{-}C_6)$alkylene group, an SO$_2$ group, an SO$_2$—$(C_1\text{-}C_6)$alkylene group, an N($R^B$)SO$_2$ group, an N($R^B$)SO$_2$—$(C_1\text{-}C_6)$alkylene group, a CO group, a CO—$(C_1\text{-}C_6)$alkylene group, an N($R^B$)CO group, an N($R^B$)CO—$(C_1\text{-}C_6)$alkylene group, an SO$_2$N($R^B$)CO group, an SO$_2$N($R^B$)CO—$(C_1\text{-}C_6)$alkylene group, an SO$_2$N($R^B$)CON($R^A$) group or an SO$_2$N($R^B$)CON($R^A$)—$(C_1\text{-}C_6)$alkylene group;

$R^A$ and $R^B$ represent, independently of one another, a hydrogen atom or a $(C_1\text{-}C_6)$alkyl group;

m and n represent, independently of one another, an integer equal to 0 or 1, in the form of the base or of an addition salt with an acid.

The compounds of formula (I) can comprise one or more asymmetric carbon atoms. They can thus exist in the form of enantiomers or diastereoisomers. These enantiomers, diastereoisomers and their mixtures, including racemic mixtures, come within the invention.

The compounds of formula (I) can exist in the form of bases or of addition salts with acids. Such addition salts come within the invention.

These salts can be prepared with pharmaceutically acceptable acids but the salts of other acids, for example of use in the purification or the isolation of the compounds of formula (I), also come within the invention.

In the context of the present invention:

$C_t\text{-}C_z$, where t and z can take their values from 1 to 7, is understood to mean a carbon chain or ring which can have from t to z carbon atoms; for example, $C_1\text{-}C_3$ can characterize a carbon chain having from 1 to 3 carbon atoms;

a halogen is understood to mean a fluorine, a chlorine, a bromine or an iodine;

an alkyl group is understood to mean a saturated, linear, branched or cyclized, aliphatic group optionally substituted by a saturated, linear, branched or cyclized, alkyl group. Mention may be made, by way of examples, of the methyl, ethyl, propyl, isopropyl, butyl, isobutyl, tert-butyl, cyclopropyl, cyclobutyl, cyclopentyl, cyclohexyl, methylcyclopropyl and cyclopropylmethyl groups, and the like;

an alkylene group is understood to mean a saturated, linear, branched or cyclized, divalent aliphatic group. By way of example, a $(C_1\text{-}C_6)$alkylene group represents a linear, branched or cyclized divalent carbon chain of 1 to 6 carbon atoms, such as a methylenyl (—CH$_2$—), an ethylenyl (—CH$_2$CH$_2$—), a 1-methylethylenyl (—CH(CH$_3$)CH$_2$—), a propylenyl (—CH$_2$CH$_2$CH$_2$—), a cyclopropylenyl (-(c-prop)), and the like;

an alkenyl group is understood to mean a mono- or poly-unsaturated, linear or branched, aliphatic group comprising, for example, one or two ethylenical unsaturations;

an alkynyl group is understood to mean a mono- or poly-unsaturated, linear or branched, aliphatic group comprising, for example, one or two ethynylic unsaturations;

an alkoxy group is understood to mean an —O-alkyl radical where the alkyl group is as defined above;

an alkylthio group is understood to mean an —S-alkyl radical where the alkyl group is as defined above;

a haloalkyl group is understood to mean an alkyl group, one or more hydrogen atoms of which have been replaced by one or more identical or different halogen atoms. Mention may be made, by way of examples, of the CF$_3$, CH$_2$CF$_3$, CHF$_2$ and CCl$_3$ groups;

a halo($C_1\text{-}C_6$)alkoxy is understood to mean an —O-alkyl radical where the alkyl group is as defined above and which is substituted by one or more identical or different halogen atoms. Mention may be made, by way of examples, of the —OCF$_3$, —OCHF$_2$ and —OCCl$_3$ groups;

an aryl group is understood to mean an aromatic cyclic group comprising between 6 and 10 carbon atoms. Mention may be made, as examples of the aryl groups, of phenyl or naphthyl; this aryl group can also exist in the partially unsaturated form; mention may be made, as examples, of an indenyl, indanyl or tetralinyl group;

a heteroaryl group is understood to mean a mono- or bicyclic group comprising from 5 to 10 atoms, including from 1 to 5 heteroatoms chosen from N, O and S, this group being aromatic, unsaturated or partially unsaturated or partially oxidized. Mention may be made, as examples of monocyclic heteroaryl groups, of: pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine. Mention may be made, as examples of bicyclic heteroaryl groups, of furofuran, thienothiophene, pyrrolopyrrole, pyrroloimidazole, pyrrolopyrazole, pyrrolotriazole, imidazoimidazole, imidazopyrazole, furopyrrole, furoimidazole, furopyrazole, furotriazole, pyrrolooxazole, imidazooxazole, pyrazolooxazole, furooxazole, oxazolooxazole, oxazoloisoxazole, pyrroloisoxazole, imidazoisoxazole, pyrazoloisoxazole, isoxazoloisoxazole, furoisoxazole, isoxazolooxadiazole, pyrrolooxadiazole, furooxadiazole, isoxazolooxadiazole, thienopyrrole, thienoimidazole, thienopyrazole, thienotriazole, pyrrolothiazole, imidazothiazole, pyrazolothiazole, triazolothiazole, furothiazole, oxazolothiazole, oxazoloisothiazole, pyrroloisothiazole, imidazoisothiazole, pyrazoloisothiazole, isoxazoloisothiazole, furoisothiazole, pyrrolothiadiazole, imidazothiadiazole, furothiadiazole, isoxazolothiadiazole, oxazolothiadiazole, isothiazolothiadiazole, indole, isoindole, benzimidazole, indazole, indolizine, benzofuran, isobenzofuran, benzothiophene, pyrrolopyridine, imidazopyridine, pyrazolopyridine, triazolopyridine, tetrazolopyridine, pyrrolopyrimidine, imidazopyrimidine, pyrazolopyrimidine, pyrrolopyrazine, imidazopyrazine, pyrazolopyrazine, pyrrolopyridazine, imidazopyridazine, pyrazolopyridazine, triazolopyridazine, pyrrolotriazine, furopyridine, furopyrimidine, furopyrazine, furopyridazine, furotriazine, oxazolopyridine, oxazolopyrimidine, oxazolopyrazine, oxazolopyridazine, isoxazolopyridine, isoxazolopyrimidine, isoxazolopyrazine, isoxazolopyridazine, oxadiazolopyridine, benzoxazole, benzisoxazole, benzoxadiazole, benzoxazine, benzodioxole, benzodioxine, benzodioxepine, thienopyridine, thienopyrimidine, thienopyrazine, thienopyridazine, thienotriazine, thiazolopyridine, thiazolopyrimidine, thiazolopyrazine, thiazolopyridazine, isothiazolopyridine, isothiazolopyrimidine, isothiazolopyrazine, isothiazolopyridazine, thiadiazolopyridine, thiadiazolopyrimidine, benzothiazole, benzisothiazole, benzothiadiazole, quinoline, isoquinoline, cinnoline, phthalazine, quinoxaline, quinazoline, naphthyridine, benzotriazine, pyridopyrimidine, pyridopyrazine, pyridopyridazine, pyridotriazine, pyrimidopyrimidine, pyrimidopyrazine, pyrimidopyridazine, pyrazinopyrazine, pyrazinopyridazine, pyrazinotriazine or pyridazinopyridazine.

These groups can exist in the unsaturated or partially unsaturated form; mention may be made, by way of examples, of: dihydrobenzofuran, dihydrobenzothiophene, tetrahydroquinoline, tetrahydroisoquinoline, indoline, dihydrobenzoxazine or dihydrobenzodioxane.

a heterocycle group is understood to mean a saturated 3- to 7-membered cyclic group comprising from 1 to 4 heteroatoms chosen from N, O and S. Mention may be made, by way of examples, of the pyrrolidine, piperidine, morpholine, piperazine, aziridine, azetidine, azepine, thiomorpholine, N-methylpiperazine, homopiperazine, azetidin-2-one, 1,2-thiazetidine 1,1-dioxide, pyrrolidin-2-one, 1,2-isothiazolidine 1,1-dioxide, piperidin-2-one, 1,2-thiazinane 1,1-dioxide, imidazolidin-2-one, oxazolidin-2-one, 1,2,5-thiadiazolidine 1,1-dioxide, 1,2,3-oxathiazolidine 2,2-dioxide, tetrahydropyrimidin-2-one, 1,3-oxazinan-2-one, 1,2,6-thiadiazinane 1,1-dioxide, 1,2,3-oxathiazinane 2,2-dioxide, piperazin-2-one, morpholin-3-one, 1,2,5-thiadiazinane 1,1-dioxide or 1,3,4-oxathiazinane 3,3-dioxide groups.

In the context of the present invention, the R, Z and A groups are read from left to right; the left part of the Z group is connected to the "R" group and the right part of "Z" is connected to the "A" group; likewise, the left part of the "A" group is connected to the "Z" group and the right part of "A" is connected to the ring system:

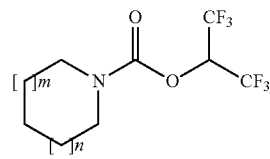

In the various groups as defined below, the A, Z, R, $R^A$, $R^B$, $R^1$, $R^2$ or $R^3$ groups, when they are not defined, have the same definitions as those mentioned above.

Among the compounds of formula (I) which are subject-matters of the invention, a first group of compounds is composed of the compounds for which:

$R^1$ represents a phenyl, naphthyl, indanyl, benzoxazole, benzisoxazole, benzimidazole, benzotriazole, oxadiazole, indazole, isoxazole, pyridine, pyrazine, pyrimidine, thienyl, thiazole, benzothiophene, indole, dihydrobenzodioxane, benzothiadiazole, pyrazole, dihydrobenzoxazine or indoline group;

$R^2$ represents one or more groups chosen from a halogen atom or a methyl, trifluoromethyl, methoxy, trifluoromethoxy, cyano, oxo, $CH_3NHCO$, $CH_3SO_2$, $NH_2CO$, $NH_2SO_2$ or pyrrolidine-$SO_2$ group;

$R^3$ represents a group chosen from a phenyl or an oxazole; and also the compound 2,2,2-trifluoro-1-(trifluoromethyl)ethyl 4-{[3-(2-methylpyrimidin-4-yl)benzenesulphonylamino]methyl}piperidine-1-carboxylate.

Among the compounds of formula (I) which are subject-matter of the invention, a second group of compounds is composed of the compounds of formula (I) for which:

Z represents a bond or a $CH_2$, $(CH_2)_2$, CH=CH, CC, $OCH_2$ or $OC(CH_3)_2$ group.

Among the compounds of formula (I) which are subject-matter of the invention, a third group of compounds is composed of the compounds of formula (I) for which:

A represents a bond, an oxygen atom, a sulphur atom, an $OCH_2$ group, an $O(CH_2)_2$ group, an NH, $NHCH_2$ or $NH(CH_2)_2$ group, an $SO_2$ or CO group, a CONH group, a $CONHCH_2$ or $CONH(CH_2)_2$ group, an $SO_2NH$ group, an $SO_2NHCH_2$ or $SO_2NH(CH_2)_2$ group, an $SO_2NHCO$, $SO_2NHCONH$ or $SO_2NHCONHCH_2$ group, an OCONH group, an NHCONH group, an $NHCONHCH_2$ group, an N(CH₃)CONHCH₂, NHCONH(CH₂)₂ or N(CH₃)CONH (CH₂)₂ group or an SO₂N(CH₃)CH₂ group.

Among the compounds of formula (I) which are subject-matter of the invention, a fourth group of compounds is composed of the compounds of formula (I) for which:
m and n represent 1.

Among the compounds of formula (I) which are subject-matters of the invention, a fifth group of compounds is composed of the compounds of formula (I) for which:
m represents 1 and n represents 0.

Among the compounds of formula (I) which are subject-matters of the invention, a sixth group of compounds is composed of the compounds of formula (I) for which:
m and n represent 0.

Among the compounds of formula (I) which are subject-matters of the invention, a seventh group of compounds is composed of the compounds of formula (I) for which:
$R^1$ represents a phenyl, naphthyl, indanyl, benzoxazole, benzisoxazole, benzimidazole, benzotriazole, oxadiazole, indazole, isoxazole, pyridine, pyrazine, pyrimidine, thienyl, thiazole, benzothiophene, indole, dihydrobenzodioxane, benzothiadiazole, pyrazole, dihydrobenzoxazine or indoline group;
$R^2$ represents one or more groups chosen from a halogen atom or a methyl, trifluoromethyl, methoxy, trifluoromethoxy, cyano, oxo, CH₃NHCO, CH₃SO₂, NH₂CO, NH₂SO₂ or pyrrolidine-SO₂ group;
$R^3$ represents a group chosen from a phenyl or an oxazole;
Z represents a bond or a CH₂, (CH₂)₂, CH=CH, C≡C, OCH₂ or OC(CH₃)₂ group;
A represents a bond, an oxygen atom, a sulphur atom, an OCH₂ group, an O(CH₂)₂ group, an NH, NHCH₂ or NH(CH₂)₂ group, an SO₂ or CO group, a CONH group, a CONHCH₂ or CONH(CH₂)₂ group, an SO₂NH group, an SO₂NHCH₂, SO₂NH(CH₂)₂ or SO₂NHC[CH₂]₂ group, an SO₂NHCO, SO₂NHCONH or SO₂NHCONHCH₂ group, an OCONH group, an NHCONH group, an NHCONHCH₂ group, an N(CH₃)CONHCH₂, NHCONH(CH₂)₂ or N(CH₃)CONH(CH₂)₂ group or an SO₂N(CH₃)CH₂ group;
m and n represent, independently of one another, an integer equal to 0 or 1, in the form of the base or of an addition salt with an acid.

The combinations of the groups one to seven as defined above also come within the invention.

Mention may in particular be made, among the compounds of formula (I) which are subject-matters of the invention, of the following compounds:

2,2,2-Trifluoro-1-(trifluoromethyl)ethyl 4-(4-chlorophenyl) piperidine-1-carboxylate
2,2,2-Trifluoro-1-(trifluoromethyl)ethyl 4-(m-tolyl)piperidine-1-carboxylate
2,2,2-Trifluoro-1-(trifluoromethyl)ethyl 4-(2-(trifluoromethyl)phenyl)piperidine-1-carboxylate
2,2,2-Trifluoro-1-(trifluoromethyl)ethyl 4-(2-methoxyphenyl)piperidine-1-carboxylate
2,2,2-Trifluoro-1-(trifluoromethyl)ethyl 4-(4-cyanophenyl) piperidine-1-carboxylate
2,2,2-Trifluoro-1-(trifluoromethyl)ethyl 4-(4-(methylcarbamoyl)phenyl)piperidine-1-carboxylate
2,2,2-Trifluoro-1-(trifluoromethyl)ethyl 4-(naphth-1-yl)piperidine-1-carboxylate
2,2,2-Trifluoro-1-(trifluoromethyl)ethyl 4-(benzoxazol-2-yl)piperidine-1-carboxylate
2,2,2-Trifluoro-1-(trifluoromethyl)ethyl 4-(5-fluorobenz[d]isoxazol-3-yl)piperidine-1-carboxylate
2,2,2-Trifluoro-1-(trifluoromethyl)ethyl 4-(6-fluorobenz[d]isoxazol-3-yl)piperidine-1-carboxylate
2,2,2-Trifluoro-1-(trifluoromethyl)ethyl 4-(2-oxo-2,3-dihydrobenzoimidazol-1-yl)-piperidine-1-carboxylate
2,2,2-Trifluoro-1-(trifluoromethyl)ethyl 4-(5-chloro-2-oxo-2,3-dihydrobenzoimidazol-1-yl)piperidine-1-carboxylate
2,2,2-Trifluoro-1-(trifluoromethyl)ethyl 4-(5-(trifluoromethyl)benzotriazol-1-yl)piperidine-1-carboxylate
2,2,2-Trifluoro-1-(trifluoromethyl)ethyl 4-[5-(4-fluorophenyl)-1,3,4-oxadiazol-2-yl]piperidine-1-carboxylate
2,2,2-Trifluoro-1-(trifluoromethyl)ethyl 4-(6-fluoro-1H-indazol-3-yl)piperidine-1-carboxylate
2,2,2-Trifluoro-1-(trifluoromethyl)ethyl 4-(benzyl)piperidine-1-carboxylate
2,2,2-Trifluoro-1-(trifluoromethyl)ethyl 4-[3-(4-chlorophenyl)isoxazol-5-ylmethyl]piperidine-1-carboxylate
2,2,2-Trifluoro-1-(trifluoromethyl)ethyl 4-[2-(4-chlorophenyl)ethyl]piperidine-1-carboxylate
2,2,2-Trifluoro-1-(trifluoromethyl)ethyl 4-(4-chlorophenylethynyl)piperidine-1-carboxylate
2,2,2-Trifluoro-1-(trifluoromethyl)ethyl 3-(4'-fluorobiphenyl-3-yloxy)azetidine-1-carboxylate
2,2,2-Trifluoro-1-(trifluoromethyl)ethyl 3-(3'-cyanobiphenyl-3-yloxy)azetidine-1-carboxylate
2,2,2-Trifluoro-1-(trifluoromethyl)ethyl (S)-3-(4'-fluorobiphenyl-3-yloxy)pyrrolidine-1-carboxylate
2,2,2-Trifluoro-1-(trifluoromethyl)ethyl (R)-3-(4'-fluorobiphenyl-3-yloxy)pyrrolidine-1-carboxylate
2,2,2-Trifluoro-1-(trifluoromethyl)ethyl (S)-3-(3'-cyanobiphenyl-3-yloxy)pyrrolidine-1-carboxylate
2,2,2-Trifluoro-1-(trifluoromethyl)ethyl (R)-3-(3'-cyanobiphenyl-3-yloxy)pyrrolidine-1-carboxylate
2,2,2-Trifluoro-1-(trifluoromethyl)ethyl 4-(4-fluorophenoxy)piperidine-1-carboxylate
2,2,2-Trifluoro-1-(trifluoromethyl)ethyl 4-(4-carbamoylphenoxy)piperidine-1-carboxylate
2,2,2-Trifluoro-1-(trifluoromethyl)ethyl 4-(3'-fluorobiphenyl-3-yloxy)piperidine-1-carboxylate
2,2,2-Trifluoro-1-(trifluoromethyl)ethyl 4-(4'-fluorobiphenyl-3-yloxy)piperidine-1-carboxylate
2,2,2-Trifluoro-1-(trifluoromethyl)ethyl 4-(3'-chlorobiphenyl-3-yloxy)piperidine-1-carboxylate
2,2,2-Trifluoro-1-(trifluoromethyl)ethyl 4-(4'-chlorobiphenyl-3-yloxy)piperidine-1-carboxylate
2,2,2-Trifluoro-1-(trifluoromethyl)ethyl 4-(3'-cyanobiphenyl-3-yloxy)piperidine-1-carboxylate
2,2,2-Trifluoro-1-(trifluoromethyl)ethyl 4-(4'-cyanobiphenyl-3-yloxy)piperidine-1-carboxylate
2,2,2-Trifluoro-1-(trifluoromethyl)ethyl 4-(3'-cyanobiphenyl-4-yloxy)piperidine-1-carboxylate
2,2,2-Trifluoro-1-(trifluoromethyl)ethyl 4-(4'-cyanobiphenyl-4-yloxy)piperidine-1-carboxylate
2,2,2-Trifluoro-1-(trifluoromethyl)ethyl 4-(3'-methoxybiphenyl-3-yloxy)piperidine-1-carboxylate
2,2,2-Trifluoro-1-(trifluoromethyl)ethyl 4-(4'-methoxybiphenyl-3-yloxy)piperidine-1-carboxylate
2,2,2-Trifluoro-1-(trifluoromethyl)ethyl 4-(4-chloronaphth-1-yloxy)piperidine-1-carboxylate
2,2,2-Trifluoro-1-(trifluoromethyl)ethyl 4-(naphth-2-yloxy)piperidine-1-carboxylate
2,2,2-Trifluoro-1-(trifluoromethyl)ethyl 4-(6-cyanonaphth-2-yloxy)piperidine-1-carboxylate
2,2,2-Trifluoro-1-(trifluoromethyl)ethyl 4-(6-methoxynaphth-2-yloxy)piperidine-1-carboxylate
2,2,2-Trifluoro-1-(trifluoromethyl)ethyl 4-(7-methoxynaphth-2-yloxy)piperidine-1-carboxylate
2,2,2-Trifluoro-1-(trifluoromethyl)ethyl 4-(pyridin-4-yloxy)piperidine-1-carboxylate 2,2,2-Trifluoro-1-(trifluoromethyl)ethyl 4-[6-(3-cyanophenyl)pyridin-2-yloxy]piperidine-1-carboxylate
2,2,2-Trifluoro-1-(trifluoromethyl)ethyl 4-[5-(3-cyanophenyl)pyridin-3-yloxy]piperidine-1-carboxylate
2,2,2-Trifluoro-1-(trifluoromethyl)ethyl 4-[6-(3-cyanophenyl)pyrimidin-4-yloxy]piperidine-1-carboxylate
2,2,2-Trifluoro-1-(trifluoromethyl)ethyl 4-[6-(4-fluorophenyl)pyrazin-2-yloxy]piperidine-1-carboxylate
2,2,2-Trifluoro-1-(trifluoromethyl)ethyl 4-[6-(3-cyanophenyl)pyrazin-2-yloxy]piperidine-1-carboxylate
2,2,2-Trifluoro-1-(trifluoromethyl)ethyl 4-(4-chloronaphth-1-yloxymethyl)piperidine-1-carboxylate
2,2,2-Trifluoro-1-(trifluoromethyl)ethyl 4-(3'-cyanobiphenyl-3-yloxymethyl)piperidine-1-carboxylate
2,2,2-Trifluoro-1-(trifluoromethyl)ethyl 4-(4'-cyanobiphenyl-3-yloxymethyl)piperidine-1-carboxylate
2,2,2-Trifluoro-1-(trifluoromethyl)ethyl 4-(3'-cyanobiphenyl-4-yloxymethyl)piperidine-1-carboxylate
2,2,2-Trifluoro-1-(trifluoromethyl)ethyl 4-(4'-cyanobiphenyl-4-yloxymethyl)piperidine-1-carboxylate
2,2,2-Trifluoro-1-(trifluoromethyl)ethyl 4-(naphth-2-yloxymethyl)piperidine-1-carboxylate
2,2,2-Trifluoro-1-(trifluoromethyl)ethyl 4-(6-methoxynaphth-2-yloxymethyl)piperidine-1-carboxylate
2,2,2-Trifluoro-1-(trifluoromethyl)ethyl 4-(7-methoxynaphth-2-yloxymethyl)piperidine-1-carboxylate
2,2,2-Trifluoro-1-(trifluoromethyl)ethyl 4-(6-cyanonaphth-2-yloxymethyl)piperidine-1-carboxylate
2,2,2-Trifluoro-1-(trifluoromethyl)ethyl 4-[2-(biphenyl-4-yloxy)ethyl]-piperidine-1-carboxylate
2,2,2-Trifluoro-1-(trifluoromethyl)ethyl 4-[2-(4-chloronaphth-1-yloxy)ethyl]piperidine-1-carboxylate
2,2,2-Trifluoro-1-(trifluoromethyl)ethyl 4-(6-bromopyridin-2-ylamino)piperidine-1-carboxylate
2,2,2-Trifluoro-1-(trifluoromethyl)ethyl 4-(5-cyanopyridin-2-ylamino)piperidine-1-carboxylate
2,2,2-Trifluoro-1-(trifluoromethyl)ethyl 4-(5-carbamoylpyridin-2-ylamino)piperidine-1-carboxylate
2,2,2-Trifluoro-1-(trifluoromethyl)ethyl 4-(5-(trifluoromethyl)pyridin-2-ylamino)pipendine-1-carboxylate
2,2,2-Trifluoro-1-(trifluoromethyl)ethyl 4-(4-trifluoromethylpyrimidin-2-ylamino)piperidine-1-carboxylate
2,2,2-Trifluoro-1-(trifluoromethyl)ethyl 4-(2-bromopyrimidin-4-ylamino)piperidine-1-carboxylate
2,2,2-Trifluoro-1-(trifluoromethyl)ethyl 4-[6-(4-fluorophenyl)pyridin-2-ylamino]pipendine-1-carboxylate
2,2,2-Trifluoro-1-(trifluoromethyl)ethyl 4-[6-(3-cyanophenyl)pyridin-2-ylamino]piperidine-1-carboxylate
2,2,2-Trifluoro-1-(trifluoromethyl)ethyl 4-[2-(3-cyanophenyl)pyrimidin-4-ylamino]pipendine-1-carboxylate
2,2,2-Trifluoro-1-(trifluoromethyl)ethyl 4-[(6-chloropyridin-2-ylamino)methyl]pipendine-1-carboxylate
2,2,2-Trifluoro-1-(trifluoromethyl)ethyl 4-(pyridin-4-ylsulphanyl)piperidine-1-carboxylate
2,2,2-Trifluoro-1-(trifluoromethyl)ethyl 4-(benzenesulphonyl)piperidine-1-carboxylate
2,2,2-Trifluoro-1-(trifluoromethyl)ethyl 4-(4-fluorobenzoyl)piperidine-1-carboxylate
2,2,2-Trifluoro-1-(trifluoromethyl)ethyl 4-(4-chlorobenzoyl)piperidine-1-carboxylate
2,2,2-Trifluoro-1-(trifluoromethyl)ethyl 4-(4-chlorobenzoylamino)piperidine-1-carboxylate
2,2,2-Trifluoro-1-(trifluoromethyl)ethyl 4-(4-methylbenzoylamino)piperidine-1-carboxylate
2,2,2-Trifluoro-1-(trifluoromethyl)ethyl 4-[(3-chlorobenzo[b]thiophene-2-carbonyl)amino]pipendine-1-carboxylate
2,2,2-Trifluoro-1-(trifluoromethyl)ethyl 4-[2-(4-chlorophenoxy)acetylamino]pipendine-1-carboxylate
2,2,2-Trifluoro-1-(trifluoromethyl)ethyl 3-[(E)-(3-phenylacryloyl)amino]azetidine-1-carboxylate
2,2,2-Trifluoro-1-(trifluoromethyl)ethyl 4-[(E)-(3-phenylacryloyl)amino]pipendine-1-carboxylate
2,2,2-Trifluoro-1-(trifluoromethyl)ethyl 4-[(4-chlorobenzoylamino)methyl]pipendine-1-carboxylate
2,2,2-Trifluoro-1-(trifluoromethyl)ethyl 4-{[(3-chlorobenzo[b]thiophene-2-carbonyl)amino]methyl}pipendine-1-carboxylate
2,2,2-Trifluoro-1-(trifluoromethyl)ethyl 4-{[2-(4-chlorophenoxy)acetylamino]methyl}piperidine-1-carboxylate
2,2,2-Trifluoro-1-(trifluoromethyl)ethyl 4-{[2-(4-chlorophenoxy)-2-methylpropionylamino]methyl}piperidine-1-carboxylate
2,2,2-Trifluoro-1-(trifluoromethyl)ethyl 3-{[(E)-(3-phenylacryloyl)amino]methyl}pyrrolidine-1-carboxylate
2,2,2-Trifluoro-1-(trifluoromethyl)ethyl 4-{[(E)-(3-phenylacryloyl)amino]methyl}piperidine-1-carboxylate
2,2,2-Trifluoro-1-(trifluoromethyl)ethyl 3-{[2-(4-chlorophenoxy)acetylamino]methyl}pyrrolidine-1-carboxylate
2,2,2-Trifluoro-1-(trifluoromethyl)ethyl 3-(2-(phenylacetylamino)ethyl)azetidine-1-carboxylate
2,2,2-Trifluoro-1-(trifluoromethyl)ethyl 3-{2-[2-(4-chlorophenoxy)acetylamino]ethyl}azetidine-1-carboxylate
2,2,2-Trifluoro-1-(trifluoromethyl)ethyl 3-{2-[(E)-(3-phenylacryloyl)amino]ethyl}azetidine-1-carboxylate
2,2,2-Trifluoro-1-(trifluoromethyl)ethyl 3-(5-bromo-2-methoxybenzenesulphonylamino)azetidine-1-carboxylate
2,2,2-Trifluoro-1-(trifluoromethyl)ethyl 3-(4-bromo-2-fluorobenzenesulphonylamino)azetidine-1-carboxylate
2,2,2-Trifluoro-1-(trifluoromethyl)ethyl 3-(indane-5-sulphonylamino)azetidine-1-carboxylate
2,2,2-Trifluoro-1-(trifluoromethyl)ethyl 3-(biphenyl-4-sulphonylamino)azetidine-1-carboxylate
2,2,2-Trifluoro-1-(trifluoromethyl)ethyl 3-(4-methylnaphthalene-1-sulphonylamino)azetidine-1-carboxylate
2,2,2-Trifluoro-1-(trifluoromethyl)ethyl 3-(5-chlorothiophene-2-sulphonylamino)azetidine-1-carboxylate
2,2,2-Trifluoro-1-(trifluoromethyl)ethyl 3-(5-bromothiophene-2-sulphonylamino)azetidine-1-carboxylate
2,2,2-Trifluoro-1-(trifluoromethyl)ethyl 3-[(benzo[b]thiophene-2-carbonyl)amino]azetidine-1-carboxylate
2,2,2-Trifluoro-1-(trifluoromethyl)ethyl 4-(3-chlorobenzenesulphonylamino)piperidine-1-carboxylate
2,2,2-Trifluoro-1-(trifluoromethyl)ethyl 4-(4-chlorobenzenesulphonylamino)piperidine-1-carboxylate
2,2,2-Trifluoro-1-(trifluoromethyl)ethyl 4-(5-bromo-2-methoxybenzenesulphonylamino)piperidine-1-carboxylate
2,2,2-Trifluoro-1-(trifluoromethyl)ethyl 4-(naphthalene-1-sulphonylamino)piperidine-1-carboxylate
2,2,2-Trifluoro-1-(trifluoromethyl)ethyl 4-(naphthalene-2-sulphonylamino)piperidine-1-carboxylate
2,2,2-Trifluoro-1-(trifluoromethyl)ethyl 3-(phenylmethanesulphonylamino)azetidine-1-carboxylate
2,2,2-Trifluoro-1-(trifluoromethyl)ethyl 4-(phenylmethanesulphonylamino)piperidine-1-carboxylate
2,2,2-Trifluoro-1-(trifluoromethyl)ethyl 3-[(4-chlorobenzenesulphonylamino)methyl]azetidine-1-carboxylate
2,2,2-Trifluoro-1-(trifluoromethyl)ethyl 3-[(3-chlorobenzenesulphonylamino)methyl]pyrrolidine-1-carboxylate
2,2,2-Trifluoro-1-(trifluoromethyl)ethyl 3-[(4-chlorobenzenesulphonylamino)methyl]pyrrolidine-1-carboxylate
2,2,2-Trifluoro-1-(trifluoromethyl)ethyl 3-[(naphthalene-1-sulphonylamino)methyl]pyrrolidine-1-carboxylate 2,2,2-Trifluoro-1-(trifluoromethyl)ethyl 3-[(naphthalene-2-sulphonylamino)methyl]pyrrolidine-1-carboxylate 2,2,2-Trifluoro-1-(trifluoromethyl)ethyl 4-((benzenesulphonylamino)methyl)piperidine-1-carboxylate 2,2,2-Trifluoro-1-(trifluoromethyl)ethyl 4-[(4-fluorobenzenesulphonylamino)methyl]pipendine-1-carboxylate 2,2,2-Trifluoro-1-(trifluoromethyl)ethyl 4-[(2-chlorobenzenesulphonylamino)methyl]pipendine-1-carboxylate 2,2,2-Trifluoro-1-(trifluoromethyl)ethyl 4-[(3-chlorobenzenesulphonylamino)methyl]piperidine-1-carboxylate 2,2,2-Trifluoro-1-(trifluoromethyl)ethyl 4-[(4-chlorobenzenesulphonylamino)-methyl]-pipendine-1-carboxylate 2,2,2-Trifluoro-1-(trifluoromethyl)ethyl 4-[(toluene-2-sulphonylamino)methyl]pipendine-1-carboxylate 2,2,2-Trifluoro-1-(trifluoromethyl)ethyl 4-[(toluene-3-sulphonylamino)methyl]piperidine-1-carboxylate 2,2,2-Trifluoro-1-(trifluoromethyl)ethyl 4-[(toluene-4-sulphonylamino)methyl]piperidine-1-carboxylate 2,2,2-Trifluoro-1-(trifluoromethypethyl 4-[(3-(trifluoromethyl)benzenesulphonylamino)-methyl]piperidine-1-carboxylate 2,2,2-Trifluoro-1-(trifluoromethyl)ethyl 4-[(4-(trifluoromethyl)benzenesulphonylamino)methyl]piperidine-1-carboxylate 2,2,2-Trifluoro-1-(trifluoromethyl)ethyl 4-[(3-methoxybenzenesulphonylamino)methyl]piperidine-1-carboxylate 2,2,2-Trifluoro-1-(trifluoromethyl)ethyl 4-[(4-methoxybenzenesulphonyl-amino)methyl]piperidine-1-carboxylate 2,2,2-Trifluoro-1-(trifluoromethyl)ethyl 4-[(3-{trifluoromethoxy}benzenesulphonylamino)methyl]piperidine-1-carboxylate 2,2,2-Trifluoro-1-(trifluoromethyl)ethyl 4-[(4-{trifluoromethoxy}benzenesulphonylamino)methyl]piperidine-1-carboxylate 2,2,2-Trifluoro-1-(trifluoromethyl)ethyl 4-[(4-fluoro-2-{trifluoromethyl}benzenesulphonyl-amino)methyl]piperidine-1-carboxylate 2,2,2-Trifluoro-1-(trifluoromethyl)ethyl 4-[(4-cyanobenzenesulphonylamino)methyl]piperidine-1-carboxylate 2,2,2-Trifluoro-1-(trifluoromethyl)ethyl 4-[(3-fluoro-4-methylbenzenesulphonyl-amino)methyl]piperidine-1-carboxylate 2,2,2-Trifluoro-1-(trifluoromethyl)ethyl 4-[(3,4-difluorobenzenesulphonyl-amino)methyl]piperidine-1-carboxylate 2,2,2-Trifluoro-1-(trifluoromethypethyl[(3,4-dichlorobenzenesulphonyl-amino)methyl]piperidine-1-carboxylate 2,2,2-Trifluoro-1-(trifluoromethyl)ethyl 4-[(3-chloro-4-methylbenzenesulphonyl-amino)methyl]piperidine-1-carboxylate 2,2,2-Trifluoro-1-(trifluoromethyl)ethyl 4-[(3-chloro-4-{trifluoromethoxy}benzene-sulphonylamino)methyl]piperidine-1-carboxylate 2,2,2-Trifluoro-1-(trifluoromethyl)ethyl 4-[(3,4-dimethylbenzenesulphonylamino)methyl]piperidine-1-carboxylate 2,2,2-Trifluoro-1-(trifluoromethyl)ethyl 4-[(3-fluoro-4-methoxybenzenesulphonylamino)methyl]piperidine-1-carboxylate 2,2,2-Trifluoro-1-(trifluoromethyl)ethyl 4-[(4-fluoro-3-methylbenzenesulphonyl-amino)methyl]piperidine-1-carboxylate 2,2,2-Trifluoro-1-(trifluoromethyl)ethyl 4-[(3-chloro-4-fluorobenzenesulphonylamino)methyl]piperidine-1-carboxylate 2,2,2-Trifluoro-1-(trifluoromethyl)ethyl 4-[(4-fluoro-3-methoxybenzenesulphonylamino)methyl]pipendine-1-carboxylate 2,2,2-Trifluoro-1-(trifluoromethyl)ethyl 4-[(4-fluoro-3-{trifluoromethyl}benzenesulphonylamino)methyl]pipendine-1-carboxylate 2,2,2-Trifluoro-1-(trifluoromethyl)ethyl 4-[(4-chloro-3-{trifluoromethyl}benzenesulphonylamino)methyl]pipendine-1-carboxylate 2,2,2-Trifluoro-1-(trifluoromethyl)ethyl 4-[(4-{methanesulphonyl}benzenesulphonylamino)methyl]pipendine-1-carboxylate 2,2,2-Trifluoro-1-(trifluoromethyl)ethyl 4-{[4-(pyrrolidine-1-sulphonyl)benzenesulphonylamino]methyl}pipendine-1-carboxylate 2,2,2-Trifluoro-1-(trifluoromethyl)ethyl 4-[(biphenyl-4-sulphonylamino)methyl]pipendine-1-carboxylate 2,2,2-Trifluoro-1-(trifluoromethyl)ethyl 4-[(naphthalene-1-sulphonylamino)methyl]pipendine-1-carboxylate 2,2,2-Trifluoro-1-(trifluoromethyl)ethyl 4-[(naphthalene-2-sulphonylamino)methyl]pipendine-1-carboxylate 2,2,2-Trifluoro-1-(trifluoromethyl)ethyl 4-[(3,5-dimethylisoxazole-4-sulphonylamino)methyl]pipendine-1-carboxylate 2,2,2-Trifluoro-1-(trifluoromethyl)ethyl 4-[(4-{oxazol-5-yl}benzenesulphonylamino)methyl]pipendine-1-carboxylate 2,2,2-Trifluoro-1-(trifluoromethyl)ethyl 4-[(4-chlorophenylmethanesulphonylamino)-methyl]pipendine-1-carboxylate 2,2,2-Trifluoro-1-(trifluoromethyl)ethyl 4-[1-(4-chlorobenzenesulphonylamino)cyclopropyl]pipendine-1-carboxylate 2,2,2-Trifluoro-1-(trifluoromethyl)ethyl 3-[2-(3-chlorobenzenesulphonylamino)ethyl]azetidine-1-carboxylate 2,2,2-Trifluoro-1-(trifluoromethyl)ethyl 3-[2-(4-chlorobenzenesulphonylamino)ethyl]azetidine-1-carboxylate 2,2,2-Trifluoro-1-(trifluoromethyl)ethyl 3-[2-(naphthalene-1-sulphonylamino)ethyl]azetidine-1-carboxylate 2,2,2-Trifluoro-1-(trifluoromethyl)ethyl 3-[2-(naphthalene-2-sulphonylamino)ethyl]azetidine-1-carboxylate 2,2,2-Trifluoro-1-(trifluoromethyl)ethyl 4-(phenoxycarbonylamino)piperidine-1-carboxylate 2,2,2-Trifluoro-1-(trifluoromethyl)ethyl 4-(3-phenylureido)piperidine-1-carboxylate 2,2,2-Trifluoro-1-(trifluoromethyl)ethyl 4-[3-(3-chlorophenyl)ureido]pipendine-1-carboxylate 2,2,2-Trifluoro-1-(trifluoromethyl)ethyl 4-[3-(4-chlorophenyl)ureido]pipendine-1-carboxylate 2,2,2-Trifluoro-1-(trifluoromethyl)ethyl 4-[3-(3-cyanophenyl)ureido]piperidine-1-carboxylate 2,2,2-Trifluoro-1-(trifluoromethyl)ethyl 4-[3-(4-cyanophenyl)ureido]piperidine-1-carboxylate 2,2,2-Trifluoro-1-(trifluoromethyl)ethyl 4-[3-(2,4-difluorophenyl)ureido]pipendine-1-carboxylate 2,2,2-Trifluoro-1-(trifluoromethyl)ethyl 4-[3-(2,4-dichlorophenyl)ureido]pipendine-1-carboxylate 2,2,2-Trifluoro-1-(trifluoromethyl)ethyl 4-[3-(2,5-dichlorophenyl)ureido]pipendine-1-carboxylate 2,2,2-Trifluoro-1-(trifluoromethyl)ethyl 4-[3-(5-chloro-2-methoxyphenyl)ureido]pipendine-1-carboxylate 2,2,2-Trifluoro-1-(trifluoromethyl)ethyl 4-[3-(3-carbamoylphenyl)ureido]pipendine-1-carboxylate 2,2,2-Trifluoro-1-(trifluoromethyl)ethyl 4-(3-benzylureido)piperidine-1-carboxylate 2,2,2-Trifluoro-1-(trifluoromethyl)ethyl 3-[3-(4-chlorophenyl)ureidomethyl]azetidine-1-carboxylate 2,2,2-Trifluoro-1-(trifluoromethyl)ethyl 3-[3-(3-chlorophenyl)ureidomethyl]pyrrolidine-1-carboxylate
2,2,2-Trifluoro-1-(trifluoromethyl)ethyl 3-[3-(4-chlorophenyl)ureidomethyl]pyrrolidine-1-carboxylate
2,2,2-Trifluoro-1-(trifluoromethyl)ethyl 3-[3-(4-cyanophenyl)ureidomethyl]pyrrolidine-1-carboxylate
2,2,2-Trifluoro-1-(trifluoromethyl)ethyl 4-[3-(4-chlorophenyl)ureidomethyl]pipendine-1-carboxylate
2,2,2-Trifluoro-1-(trifluoromethyl)ethyl 4-{3-[2-(4-{trifluoromethyl}phenyl)thiazol-4-yl]-ureidomethyl}piperidine-1-carboxylate
2,2,2-Trifluoro-1-(trifluoromethyl)ethyl 3-(3-benzylureidomethyl)pyrrolidine-1-carboxylate
2,2,2-Trifluoro-1-(trifluoromethyl)ethyl 4-(3-benzylureidomethyl)piperidine-1-carboxylate
2,2,2-Trifluoro-1-(trifluoromethyl)ethyl 3-(3-methyl-3-phenylureidomethyl)pyrrolidine-1-carboxylate
2,2,2-Trifluoro-1-(trifluoromethyl)ethyl 3-{2-[3-(3-chlorophenyl)ureido]ethyl}azetidine-1-carboxylate
2,2,2-Trifluoro-1-(trifluoromethyl)ethyl 3-{2-[3-(4-chlorophenyl)ureido]ethyl}azetidine-1-carboxylate
2,2,2-Trifluoro-1-(trifluoromethyl)ethyl 3-{2-[3-(4-cyanophenyl)ureido]ethyl}azetidine-1-carboxylate
2,2,2-Trifluoro-1-(trifluoromethyl)ethyl 3-[2-(3-methyl-3-phenylureido)ethyl]azetidine-1-carboxylate
2,2,2-Trifluoro-1-(trifluoromethyl)ethyl 4-{2-[3-(4-chlorophenyl)ureido]ethyl}piperidine-1-carboxylate
2,2,2-Trifluoro-1-(trifluoromethyl)ethyl 3-[2-(3-benzylureido)ethyl]azetidine-1-carboxylate
2,2,2-Trifluoro-1-(trifluoromethyl)ethyl 4-(4-chlorobenzenesulphonylamino-carbonyl)piperidine-1-carboxylate
2,2,2-Trifluoro-1-(trifluoromethyl)ethyl 4-({[(4-chlorophenyl)sulphonyl]carbamoyl}amino)piperidine-1-carboxylate
2,2,2-Trifluoro-1-(trifluoromethyl)ethyl 4-[({[(4-chlorophenyl)sulphonyl]carbamoyl}amino)methyl]piperidine-1-carboxylate
2,2,2-Trifluoro-1-(trifluoromethyl)ethyl 4-(3-carbamoylphenoxy)piperidine-1-carboxylate
2,2,2-Trifluoro-1-(trifluoromethyl)ethyl 4-(3-carbamoylphenoxymethyl)piperidine-1-carboxylate
2,2,2-Trifluoro-1-(trifluoromethyl)ethyl 4-[(indole-1-carbonyl)amino]piperidine-1-carboxylate
2,2,2-Trifluoro-1-(trifluoromethyl)ethyl 4-{[(indole-1-carbonyl)amino]methyl}piperidine-1-carboxylate
2,2,2-Trifluoro-1-(trifluoromethyl)ethyl 4-[(2-fluorobenzenesulphonylamino)methyl]piperidine-1-carboxylate
2,2,2-Trifluoro-1-(trifluoromethyl)ethyl 4-[(2-{trifluoromethyl}benzenesulphonylamino)methyl]piperidine-1-carboxylate
2,2,2-Trifluoro-1-(trifluoromethyl)ethyl 4-[(2-methoxybenzenesulphonylamino)methyl]pipendine-1-carboxylate
2,2,2-Trifluoro-1-(trifluoromethyl)ethyl 4-[(3-cyanobenzenesulphonylamino)methyl]pipendine-1-carboxylate
2,2,2-Trifluoro-1-(trifluoromethyl)ethyl 4-[(3-chloro-2-fluorobenzenesulphonylamino)methyl]pipendine-1-carboxylate
2,2,2-Trifluoro-1-(trifluoromethyl)ethyl 4-[(benzo[b]thiophene-3-sulphonylamino)methyl]pipendine-1-carboxylate
2,2,2-Trifluoro-1-(trifluoromethyl)ethyl 4-[1-(4-methoxybenzenesulphonylamino)cyclopropyl]pipendine-1-carboxylate
2,2,2-Trifluoro-1-(trifluoromethyl)ethyl 4-{2-[(1H-indol-1-ylcarbonyl)amino]ethyl}pipendine-1-carboxylate
2,2,2-Trifluoro-1-(trifluoromethyl)ethyl 4-({[3-(methylsulphonyl)phenyl]carbamoyl}amino)pipendine-1-carboxylate
2,2,2-Trifluoro-1-(trifluoromethyl)ethyl 4-{[(1H-benzimidazol-5-ylcarbamoyl)amino]methyl}pipendine-1-carboxylate
2,2,2-Trifluoro-1-(trifluoromethyl)ethyl 4-{[(1H-indazol-6-ylcarbamoyl)amino]methyl}pipendine-1-carboxylate
2,2,2-Trifluoro-1-(trifluoromethyl)ethyl 4-(4-carbamoylphenoxymethyl)piperidine-1-carboxylate
2,2,2-Trifluoro-1-(trifluoromethyl)ethyl 4-[2-(3-carbamoylphenoxy)ethyl]piperidine-1-carboxylate
2,2,2-Trifluoro-1-(trifluoromethyl)ethyl 4-[2-(4-carbamoylphenoxy)ethyl]piperidine-1-carboxylate
2,2,2-Trifluoro-1-(trifluoromethyl)ethyl 4-(4-(methanesulphonyl)benzenesulphonylamino)piperidine-1-carboxylate
2,2,2-Trifluoro-1-(trifluoromethyl)ethyl 4-(pyridine-3-sulphonylamino)piperidine-1-carboxylate
2,2,2-Trifluoro-1-(trifluoromethyl)ethyl 4-[(2-{trifluoromethoxy}benzenesulphonylamino)methyl]piperidine-1-carboxylate
2,2,2-Trifluoro-1-(trifluoromethyl)ethyl 4-[(2-methoxy-4-methylbenzenesulphonylamino)methyl]piperidine-1-carboxylate
2,2,2-Trifluoro-1-(trifluoromethyl)ethyl 4-[(2,4-dimethoxybenzenesulphonylamino)methyl]piperidine-1-carboxylate
2,2,2-Trifluoro-1-(trifluoromethyl)ethyl 4-[(2,5-dimethoxybenzenesulphonylamino)methyl]piperidine-1-carboxylate
2,2,2-Trifluoro-1-(trifluoromethyl)ethyl 4-[(5-fluoro-2-methoxybenzenesulphonylamino)methyl]piperidine-1-carboxylate
2,2,2-Trifluoro-1-(trifluoromethyl)ethyl 4-[(5-methanesulphonyl-2-methoxybenzenesulphonylamino)methyl]piperidine-1-carboxylate
2,2,2-Trifluoro-1-(trifluoromethyl)ethyl 4-[(4-chloro-2,5-dimethylbenzenesulphonylamino)methyl]piperidine-1-carboxylate
2,2,2-Trifluoro-1-(trifluoromethyl)ethyl 4-{[3-(5-methyl-1,3,4-oxadiazol-2-yl)benzenesulphonylamino]methyl}piperidine-1-carboxylate
2,2,2-Trifluoro-1-(trifluoromethyl)ethyl 4-[(2,3-dihydrobenzo[1,4]dioxine-6-sulphonylamino)methyl]piperidine-1-carboxylate
2,2,2-Trifluoro-1-(trifluoromethyl)ethyl 4-[(benzo[1,2,5]thiadiazole-4-sulphonylamino)methyl]piperidine-1-carboxylate
2,2,2-Trifluoro-1-(trifluoromethyl)ethyl 4-[(4-methyl-3,4-dihydro-2H-benzo[1,4]oxazine-7-sulphonylamino)methyl]piperidine-1-carboxylate
2,2,2-Trifluoro-1-(trifluoromethyl)ethyl 4-{[3-(2-methylpyrimidin-4-yl)benzenesulphonylamino]methyl}piperidine-1-carboxylate
2,2,2-Trifluoro-1-(trifluoromethyl)ethyl 4-[(5-chloro-1,3-dimethyl-1H-pyrazole-4-sulphonylamino)methyl]piperidine-1-carboxylate
2,2,2-Trifluoro-1-(trifluoromethyl)ethyl 4-[(pyridine-3-sulphonylamino)methyl]piperidine-1-carboxylate
2,2,2-Trifluoro-1-(trifluoromethyl)ethyl 4-[(6-chloropyridine-3-sulphonylamino)methyl]piperidine-1-carboxylate
2,2,2-Trifluoro-1-(trifluoromethyl)ethyl 4-{[N-4-(chlorobenzenesulphonyl)-N-methylamino]methyl}piperidine-1-carboxylate
2,2,2-Trifluoro-1-(trifluoromethyl)ethyl 4-[2-(4-(methanesulphonyl)benzenesulphonylamino)ethyl]piperidine-1-carboxylate 2,2,2-Trifluoro-1-(trifluoromethyl)ethyl 4-[2-(pyridine-3-sulphonylamino)ethyl]piperidine-1-carboxylate 2,2,2-Trifluoro-1-(trifluoromethyl)ethyl 3-[1-(4-chlorobenzenesulphonylamino)cyclopropyl]azetidine-1-carboxylate 2,2,2-Trifluoro-1-(trifluoromethyl)ethyl 3-[1-(5-methanesulphonyl-2-methoxybenzenesulphonylamino)cyclopropyl]azetidine-1-carboxylate 2,2,2-Trifluoro-1-(trifluoromethyl)ethyl 3-[1-(pyridine-3-sulphonylamino)cyclopropyl]azetidine-1-carboxylate 2,2,2-Trifluoro-1-(trifluoromethyl)ethyl 3-[1-(4-{methanesulphonyl}benzenesulphonylamino)cyclopropyl]azetidine-1-carboxylate 2,2,2-Trifluoro-1-(trifluoromethyl)ethyl 4-[(4-{methanesulphonyl}phenylamino)methyl]pipendine-1-carboxylate 2,2,2-Trifluoro-1-(trifluoromethyl)ethyl 4-[(4-sulfamoylphenylamino)methyl]pipendine-1-carboxylate 2,2,2-Trifluoro-1-(trifluoromethyl)ethyl 4-[(2-carbamoylpyridin-4-ylamino)methyl]piperidine-1-carboxylate 2,2,2-Trifluoro-1-(trifluoromethyl)ethyl 4-[(4-carbamoylpyridin-2-ylamino)methyl]pipendine-1-carboxylate 2,2,2-Trifluoro-1-(trifluoromethyl)ethyl 4-[(5-carbamoylpyridin-2-ylamino)methyl]pipendine-1-carboxylate 2,2,2-Trifluoro-1-(trifluoromethyl)ethyl 4-[(6-carbamoylpyridin-2-ylamino)methyl]pipendine-1-carboxylate 2,2,2-Trifluoro-1-(trifluoromethyl)ethyl 4-[(5-carbamoylpyrazin-2-ylamino)methyl]pipendine-1-carboxylate 2,2,2-Trifluoro-1-(trifluoromethyl)ethyl 4-(4-carbamoylpyrazol-1-ylmethyl)piperidine-1-carboxylate 2,2,2-Trifluoro-1-(trifluoromethyl)ethyl 4-[2-(5-carbamoylpyridin-2-ylamino)ethyl]pipendine-1-carboxylate 2,2,2-Trifluoro-1-(trifluoromethyl)ethyl 4-[2-(4-carbamoylpyrimidin-2-ylamino)ethyl]pipendine-1-carboxylate 2,2,2-Trifluoro-1-(trifluoromethyl)ethyl 4-[2-(5-carbamoylpyrazin-2-ylamino)ethyl]pipendine-1-carboxylate 2,2,2-Trifluoro-1-(trifluoromethyl)ethyl 4-[2-(6-carbamoylpyrazin-2-ylamino)ethyl]pipendine-1-carboxylate 2,2,2-Trifluoro-1-(trifluoromethyl)ethyl 4-[(2,3-dihydrobenz[1,4]oxazine-4-carbonyl)amino]piperidine-1-carboxylate 2,2,2-Trifluoro-1-(trifluoromethyl)ethyl 4-{[(2,3-dihydrobenz[1,4]oxazine-4-carbonyl)amino]methyl}pipendine-1-carboxylate 2,2,2-Trifluoro-1-(trifluoromethyl)ethyl 4-[2-(3-{methanesulphonyl}benzoylamino)ethyl]pipendine-1-carboxylate 2,2,2-Trifluoro-1-(trifluoromethyl)ethyl 4-[2-(4-{methanesulphonyl}benzoylamino)ethyl]piperidine-1-carboxylate 2,2,2-Trifluoro-1-(trifluoromethyl)ethyl 4-[2-(4-sulfamoylbenzoylamino)ethyl]piperidine-1-carboxylate 2,2,2-Trifluoro-1-(trifluoromethyl)ethyl 4-{2-[(2,3-dihydrobenz[1,4]oxazine-4-carbonyl)amino]ethyl}piperidine-1-carboxylate 2,2,2-Trifluoro-1-(trifluoromethyl)ethyl 4-[3-(1H-benzimidazol-5-yl)ureido]piperidine-1-carboxylate 2,2,2-Trifluoro-1-(trifluoromethyl)ethyl 4-[3-(1-methanesulphonyl-2,3-dihydro-1H-indol-5-yl)ureido]piperidine-1-carboxylate 2,2,2-Trifluoro-1-(trifluoromethyl)ethyl 4-[3-(1H-indazol-6-yl)ureido]piperidine-1-carboxylate 2,2,2-Trifluoro-1-(trifluoromethyl)ethyl 4-[3-(5-methanesulphonyl-2-methoxyphenyl)ureidomethyl]piperidine-1-carboxylate 2,2,2-Trifluoro-1-(trifluoromethyl)ethyl 4-{3-[2-methoxy-5-(pyrrolidine-1-sulphonyl)phenyl]ureidomethyl}piperidine-1-carboxylate 2,2,2-Trifluoro-1-(trifluoromethyl)ethyl 4-[3-(1-methanesulphonyl-2,3-dihydro-1H-indol-5-yl)ureidomethyl]piperidine-1-carboxylate In that which follows, the term "protective group Pg" is understood to mean a group which makes it possible, on the one hand, to protect a reactive functional group, such as a hydroxyl or an amine, during a synthesis and, on the other hand, to regenerate the reactive functional group intact at the end of the synthesis. Examples of protective groups and of protecting and deprotecting methods are given in "Protective Groups in Organic Synthesis", Green et al., $2^{nd}$ Edition (John Wiley & Sons Inc., New York), 1991.

The term "leaving group" is understood to mean, in that which follows, a group which can be easily cleaved from a molecule by splitting a heterolytic bond, with departure of an electron pair. This group can thus be easily replaced by another group, for example during a substitution reaction.

In accordance with the invention, the compounds of general formula (I) can be prepared according to the process which follows:

A general method (scheme 1) for the preparation of the compounds according to the invention consists in reacting an amine of general formula (II), in the base or salt form, in which m, n, A, Z and R are as defined above, with a derivative of general formula (III), in which X represents a leaving group, such as a chlorine atom, a 4-nitrophenoxy group, an imidazole group, a 1,2,4-triazole group or an N-oxysuccinimide group. The reaction is carried out in a solvent, such as dichloromethane, acetonitrile, N-methylpyrrolidinone, dimethyl sulphoxide, dimethylformamide or a mixture of these solvents, optionally in the presence of a base, such as pyridine or diisopropylethylamine, and of a catalyst, such as 4-dimethylaminopyridine, at a temperature of between 0 and 80° C.

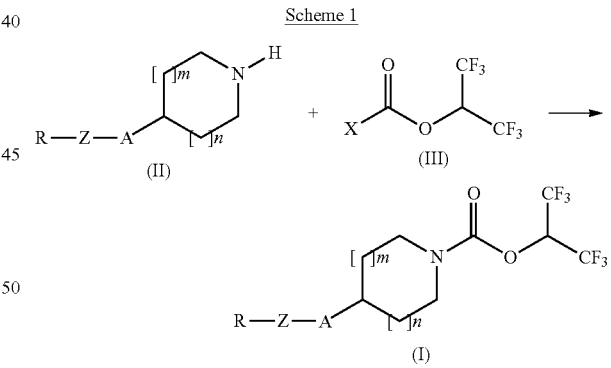

Scheme 1

The compounds of general formula (II) are available commercially or are described in the literature or can be prepared according to methods which are described therein or which are known to a person skilled in the art, as illustrated in the examples which follow.

The compounds of general formula (III) are prepared by reaction of the alcohol 1,1,1,3,3,3-hexafluoro-2-propanol with triphosgene, 4-nitrophenyl chloroformate, carbonyldiimidazole, carbonyldi(1,2,4-triazole) or carbonyldi(N-oxysuccinimide), in a solvent, such as dichloromethane, acetonitrile or N-methylpyrrolidinone, optionally in the presence of a base, such as pyridine, and of a catalyst, such as 4-dimethylaminopyridine, at a temperature of between 0 and 80° C.

The compounds (III) are generally prepared and used in situ. Some of the compounds of general formula (III) have already been reported in the literature (X=chlorine, Synthesis, 1993 (1), 103-106; X=imidazole, *Tetrahedron Letters,* 1982, 23 (20), 2113-2116; X=1,2,4-triazole, Chem. Pharm. Bull., 1983, 31 (12), 4578-4581).

Alternatively, the compounds of general formula (Ia), in which A represents a $CON(R^A)$, $CON(R^A)$—$(C_1$-$C_6)$alkylene, $SO_2N(R^A)$, $SO_2N(R^A)$—$(C_1$-$C_6)$alkylene, $N(R^B)CON(R^A)$, $N(R^B)CON(R^A)$—$(C_1$-$C_6)$alkylene, $OCON(R^A)$ or $OCON(R^A)$—$(C_1$-$C_6)$alkylene group and R, Z, m and n are as defined above, can be prepared (Scheme 2) by reacting a derivative of general formula (IV), in which W represents a carbonyl chloride (COCl), sulphonyl chloride ($SO_2Cl$), isocyanate (NCO), carbamoyl chloride ($N(R^B)COCl$) or chloroformate (OCOCl) functional group, with a derivative of general formula (V), in which V represents an amine $HN(R^A)$ or $HN(R^A)$—$(C_1$-$C_6)$alkylene functional group. This derivative of formula (V) can be:

a hexafluoroisopropyl piperidine-1-carboxylate derivative, when m and n represent 1;

a hexafluoroisopropyl pyrrolidine-1-carboxylate derivative, when m represents 1 and n represents 0;

a hexafluoroisopropyl azetidine-1-carboxylate derivative, when m and n represent 0.

Scheme 2

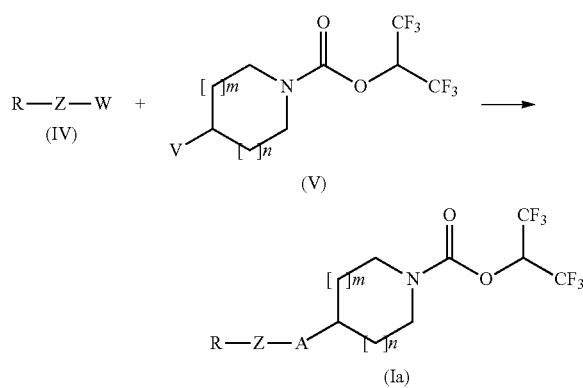

The reaction is carried out in a solvent, such as dichloromethane, acetonitrile or N-methylpyrrolidinone, optionally in the presence of a base, such as pyridine or diisopropylethylamine, and of a catalyst such as 4-dimethylaminopyridine, at a temperature between 0 and 80° C.

The compounds of general formula (IV) are commercially available or are described in the literature or can be prepared according to methods which are described therein or which are known to a person skilled in the art.

The compounds of general formula (V), in the base or salt form, are novel and come within the invention. They are of use as intermediates in the synthesis of the compounds of formula (Ia) and can be prepared as described in the examples which follow.

The examples which follow illustrate the preparation of a few compounds of the invention. These examples are not limiting and serve only to illustrate the invention. The microanalyses, the IR and NMR spectra and/or the LC/MS analyses confirm the structures and the purities of the compounds obtained. The numbers of the compounds in the examples refer to those given in the table below, in which the chemical structures and the physical properties of a few compounds according to the invention are illustrated.

The proton nuclear magnetic resonance ($^1$H NMR) spectra were recorded at 200 MHz or 400 MHz (chemical shifts δ in ppm) in $d_3$-chloroform ($CDCl_3$), $d_6$-(dimethyl sulphoxide) (DMSO) or $d_4$-methanol ($CD_3OD$). The abbreviations used to characterize the signals are as follows: s=singlet, m=multiplet, d=doublet, t=triplet, q=quartet, sept.=septet.

Examples of LC/MS analytical methods are described in detail below. The retention times (Rt) are expressed in minutes.

Method A:

HPLC/Trap—5 mM ammonium acetate/acetonitrile gradient

T0: 100% A—T13 to T16 min: 100% B—T16.5 to T20 min: 100% A Route A: ammonium acetate+3% acetonitrile; Route B: acetonitrile Flow rate: 0.5 ml/min–T°=40° C.

Column: Kromasil C18 (50*2.1 mm; 3.5 μm)

Method B:

HPLC/ZQ—water/acetonitrile/trifluoroacetic acid gradient

T0: 100% A—T13 to T16 min: 100% B—T16.5 to T20 min: 100% A

Route A: water+0.05°)/0 trifluoroacetic acid+3% acetonitrile; Route B: acetonitrile+0.035°)/0 trifluoroacetic acid Flow rate: 0.5 ml/min–T°=40° C.

Column: Kromasil C18 (50*2.1 mm; 3.5 μm)

Method C:

HPLC/ZQ—5 mM ammonium acetate/acetonitrile gradient

T0: 100% A—T5.5 to T7 min: 100% B—T7.1 to T10 min: 100% A

Route A: ammonium acetate+3% acetonitrile; Route B: acetonitrile

Flow rate: 0.8 ml/min–T°=40° C.

Column: Kromasil C18 (50*2.1 mm; 3.5 μm)

Method D:

UPLC/TOF—water/acetonitrile/trifluoroacetic acid gradient

T0: 98% A—T1.6 to T2.1 min: 100% B—T2.5 to T3 min: 98% A

Route A: water+0.05% trifluoroacetic acid; Route B: acetonitrile+0.035% trifluoroacetic acid Flow rate: 1.0 ml/min–T°=40° C.

Column: Acquity BEH C18 (50*2.1 mm; 1.7 μm)

Method E:

HPLC/TOF—water/acetonitrile/trifluoroacetic acid gradient

T0: 95% A—T2.5 min: 95% B

Route A: water+0.05% trifluoroacetic acid; Route B: acetonitrile+0.05% trifluoroacetic acid Flow rate: 1.3 ml/min—ambient temperature Column: YMC-Pack Jsphere H80 (33*2.1 mm; 4 μm)

Example 1

Compound No. 5

2,2,2-Trifluoro-1-(trifluoromethyl)ethyl 4-(4-cyanophenyl)piperidine-1-carboxylate

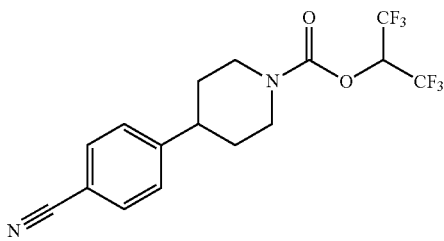 [SMILES: N#Cc1ccc(C2CCN(C(=O)OC(C(F)(F)F)C(F)(F)F)CC2)cc1]

A solution of 0.604 g (3.6 mmol) of 1,1,1,3,3,3-trifluoro-2-propanol, 0.32 ml (3.96 mmol) of pyridine and 0.014 g (0.12 mmol) of 4-dimethylaminopyridine in 9 ml of dichloromethane is added dropwise to a solution, cooled to 0° C., under an argon atmosphere, of 0.356 g (1.2 mmol) of triphosgene in 8 ml of dichloromethane. Stirring is continued at ambient temperature for 6 hours. 0.670 g (3.6 mmol) of 4-(piperidin-4-yl)benzonitrile and 1.31 ml (7.92 mmol) of diisopropylethylamine are subsequently added. The mixture is left stirring overnight. 23 ml of dichloromethane are added. The organic phase is washed 3 times with 40 ml of ice-cold water, dried over sodium sulphate and evaporated to dryness. The product is purified by chromatography on silica gel, elution being carried out with a 15:85 mixture of ethyl acetate and cyclohexane. Crystallization is carried out from n-hexane in order to obtain 0.32 g (0.84 mmol) of product in the form of a white powder.

Melting point (° C.): 54-56
LC/MS (method A): Rt 9.7 min, m/z 398 (MNH$_4$+)
IR (KBr, cm$^{-1}$): 2226, 1743
$^1$H NMR (CDCl$_3$, δ ppm, 200 MHz): 7.65 (d, 2H), 7.35 (d, 2H), 5.8 (sept., 1H), 4.35 (m, 2H), 3.05 (m, 2H), 2.8 (m, 1H), 1.95 (m, 2H), 1.8 (m, 2H).

Example 2

Compound No. 10)

2,2,2-Trifluoro-1-(trifluoromethyl)ethyl 4-(6-fluorobenz[d]isoxazol-3-yl)piperidine-1-carboxylate

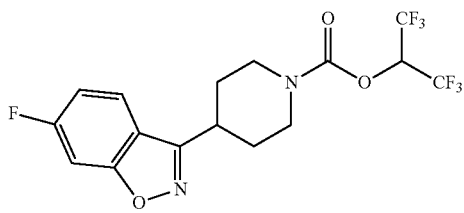 [SMILES: O=C(OC(C(F)(F)F)C(F)(F)F)N1CCC(c2noc3cc(F)ccc23)CC1]

A solution of 0.342 g (1.7 mmol) of 4-nitrophenyl chloroformate in 6 ml of dichloromethane is added dropwise to a solution, cooled to 0° C., under an argon atmosphere, of 0.571 g (3.4 mmol) of 1,1,1,3,3,3-trifluoro-2-propanol, 0.28 ml (3.4 mmol) of pyridine and 0.011 g (0.1 mmol) of 4-dimethylaminopyridine in 5 ml of dichloromethane. The mixture is stirred at ambient temperature overnight. 0.374 g (1.7 mmol) of 6-fluoro-3-(piperidin-4-yl)benz[d]isoxazole and then 0.74 ml (4.25 mmol) of diisopropylethylamine are subsequently added. The mixture is stirred at ambient temperature for 5 hours. 4 g of silica are added and the mixture is evaporated to dryness. The product is purified by chromatography on silica gel, elution being carried out with a 10:90 mixture and then a 15:85 mixture of ethyl acetate and cyclohexane. Crystallization is carried out in n-hexane in order to obtain 0.45 g (1.09 mmol) of product in the form of white crystals.

Melting point (° C.): 91-93
LC/MS (method B): Rt 10.6 min, m/z 415 (MH+)
IR (KBr, cm$^{-1}$): 1741
$^1$H NMR (DMSO, δ ppm, 200 MHz): 8.0 (d.d, 1H), 7.7 (d.d, 1H), 7.3 (d.t, 1H), 6.55 (sept., 1H), 4.05 (m, 2H), 3.5 (m, 1H), 3.2 (m, 2H), 2.1 (m, 2H), 1.75 (m, 2H).

Example 3

Compound No. 12)

2,2,2-Trifluoro-1-(trifluoromethyl)ethyl 4-(5-chloro-2-oxo-2,3-dihydrobenzimidazol-1-yl)piperidine-1-carboxylate

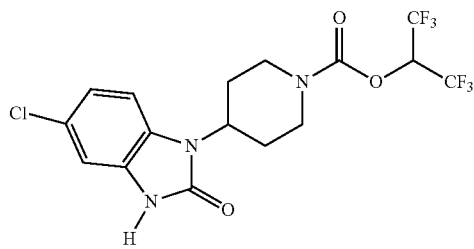 [SMILES: O=C(OC(C(F)(F)F)C(F)(F)F)N1CCC(n2c(=O)[nH]c3cc(Cl)ccc32)CC1]

0.328 g (2 mmol) of carbonyldi(1,2,4-triazole) is added to a solution of 0.6725 g (4 mmol) of 1,1,1,3,3,3-trifluoro-2-propanol and 0.012 g (0.1 mmol) of 4-dimethylaminopyridine in 10 ml of dichloromethane. The mixture is stirred at ambient temperature overnight and then 0.503 g (2 mmol) of 5-chloro-1-piperidin-4-yl-1,3-dihydrobenzimidazol-2-one is added. Stirring is continued at ambient temperature for 3 hours and the dichloromethane is evaporated under vacuum. The residue is taken up in a mixture of 50 ml of ethyl acetate and 20 ml of 1N aqueous hydrochloric acid. The organic phase is separated by settling and is then washed with 2 times 20 ml of water and then with 20 ml of a saturated aqueous sodium chloride solution. It is dried over sodium sulphate and evaporated under vacuum. The product is purified by chromatography on silica gel, elution being carried out with a 30:70, then 40:60 and 50:50 mixture of ethyl acetate and cyclohexane. Recrystallization is subsequently carried out under hot conditions for a mixture of ethyl acetate and cyclohexane in order to obtain 0.28 g (0.62 mmol) of product in the form of a white crystalline powder.

Melting point (° C.): 231-233
LC/MS (method B): Rt 9.3 min, m/z 446 (MH+)
IR (KBr, cm$^{-1}$): 1751, 1697

¹H NMR (CDCl₃, δ ppm, 200 MHz): 8.6 (s, 1H), 7.15-6.95 (m, 3H), 5.85 (sept., 1H), 4.6-4.3 (m, 3H), 3.1 (m, 2H), 2.4 (m, 2H), 1.95 (m, 2H).

Example 4

Compound No. 75

2,2,2-Trifluoro-1-(trifluoromethyl)ethyl 4-(4-chlorobenzoyl)piperidine-1-carboxylate

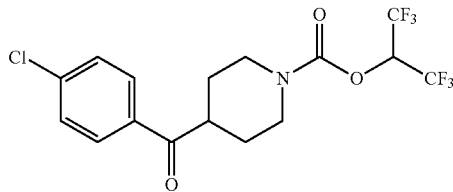 [SMILES: O=C(c1ccc(Cl)cc1)C1CCN(C(=O)OC(C(F)(F)F)C(F)(F)F)CC1]

0.512 g (2 mmol) of carbonyldi(N-oxysuccinimide) and 0.012 g (0.1 mmol) of 4-dimethylaminopyridine are added to a solution of 0.504 g (3 mmol) of 1,1,1,3,3,3-trifluoro-2-propanol in 7 ml of dichloromethane. The mixture is stirred at ambient temperature for 4 hours. It is cooled to 0° C. and 0.520 g (2 mmol) of (4-chloro-phenyl)(piperidin-4-yl)methanone hydrochloride and then 1.04 ml (6 mmol) of diisopropylethylamine are added. The mixture is stirred at ambient temperature overnight. 20 ml of ice-cold water and 50 ml of ice-cold dichloromethane are added. The organic phase is separated by settling. It is washed twice with ice-cold water and then with 20 ml of a saturated aqueous sodium chloride solution. It is dried over sodium sulphate and evaporated to dryness. The product is purified by chromatography on silica gel, elution being carried out with a 5:95 and then 10:90 mixture of ethyl acetate and cyclohexane, in order to obtain 0.175 g (0.42 mmol) of product in the form of a colourless oil.

LC/MS (method A): Rt 10.9 min, m/z 418 (MH+)
IR (film, cm⁻¹): 1739, 1684
¹H NMR (CDCl₃, δ ppm, 200 MHz): 7.8 (d, 2H), 7.4 (d, 2H), 5.7 (sept., 1H), 4.1 (d, 2H), 3.5 (m, 1H), 3.1 (m, 2H), 1.9-1.6 (m, 4H).

Example 5

Compound No. 33

2,2,2-Trifluoro-1-(trifluoromethyl)ethyl 4-(3'-cyanobiphenyl-3-yloxy)piperidine-1-carboxylate

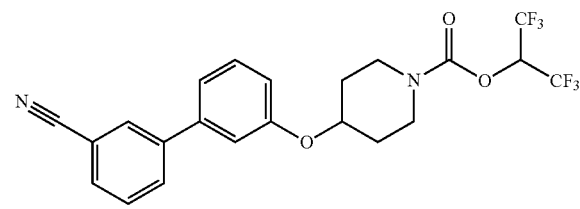 [SMILES: N#Cc1cccc(-c2cccc(OC3CCN(C(=O)OC(C(F)(F)F)C(F)(F)F)CC3)c2)c1]

5.1. tert-Butyl 4-(3'-cyanobiphenyl-3-yloxy)piperidine-1-carboxylate

A solution of 1.210 g (5.99 mmol) of diisopropyl azodicarboxylate is added dropwise to a solution, cooled to 0° C., under an argon atmosphere, of 0.974 g (4.99 mmol) of 3'-hydroxybiphenyl-3-carbonitrile, 1.205 g (5.99 mmol) of tert-butyl 4-hydroxypiperidine-1-carboxylate and 1.570 g (5.99 mmol) of triphenylphosphine in 12 ml of tetrahydrofuran. The mixture is subsequently stirred at ambient temperature overnight. 15 g of silica are added and the mixture is evaporated to dryness. The product is purified by chromatography on silica gel, elution being carried out with a 10:90 and then 15:85 mixture of ethyl acetate and cyclohexane, in order to obtain 1.538 g (4.06 mmol) of product in the form of a colourless oil.

5.2. 3'-(Piperidin-4-yloxy)biphenyl-3-carbonitrile 1.508 g (3.98 mmol) of tert-butyl 4-(3'-cyanobiphenyl-3-yloxy)piperidine-1-carboxylate obtained in stage 5.1. are dissolved in 13 ml of dichloromethane. 3.07 ml (39.84 mmol) of trifluoroacetic acid are added and the mixture is stirred at ambient temperature for 4 hours. It is evaporated to dryness and then coevaporated twice with 12 ml of 1,2-dichloroethane. The residue is taken up in a mixture of 18 ml of dichloromethane and 9 ml of a 1N aqueous sodium hydroxide solution. The organic phase is separated by settling and the aqueous phase is extracted with 12 ml of dichloromethane. The organic phases are washed with 18 ml of water and then 18 ml of a saturated aqueous sodium chloride solution. They are dried over sodium sulphate and evaporated to dryness in order to provide 1.026 g (3.68 mmol) of product in the form of an orange oil.

5.3. 2,2,2-Trifluoro-1-(trifluoromethyl)ethyl 4-(3'-cyanobiphenyl-3-yloxy)piperidine-1-carboxylate A solution of 0.504 g (3 mmol) of 1,1,1,3,3,3-hexafluoro-2-propanol, 0.27 ml (3 mmol) of pyridine and 0.012 g (0.1 mmol) of 4-dimethylaminopyridine in 6 ml of dichloromethane is added dropwise to a solution, cooled to 0° C., under an argon atmosphere, of 0.296 g (1 mmol) of triphosgene in 7 ml of dichloromethane. The mixture is stirred at ambient temperature for 5 hours. A solution of 0.835 g (3 mmol) of 3'-(piperidin-4-yloxy)biphenyl-3-carbonitrile obtained in stage 5.2. in 4.9 ml of dichloromethane and then 1.09 ml (6.6 mmol) of diisopropylethylamine are subsequently added. The mixture is stirred at ambient temperature overnight. 11 ml of dichloromethane are added and the organic phase is washed with 3 times 25 ml of ice-cold water. The organic phase is dried over sodium sulphate and evaporated to dryness. The product is purified by chromatography on silica gel, elution being carried out with a 10:90 mixture of ethyl acetate and cyclohexane. Crystallization is subsequently carried out from n-hexane in order to obtain 0.635 g (1.34 mmol) of product in the form of a white solid.

Melting point (° C.): 80-82
LC/MS (method A): Rt 11.8 min, m/z 473 (MH+)
IR (KBr, cm⁻¹): 2235, 1730
¹H NMR (CDCl₃, δ ppm, 200 MHz): 7.85 (m, 2H), 7.7-7.5 (m, 2H), 7.4 (t, 1H), 7.15 (m, 2H), 7.0 (d,d, 1H), 5.8 (sept., 1H), 4.65 (m, 1H), 3.85-3.55 (m, 4H), 2.0 (m, 4H).

Example 6

Compound No. 65

2,2,2-Trifluoro-1-(trifluoromethyl)ethyl 4-(5-(trifluoromethyl)pyridin-2-ylamino)piperidine-1-carboxylate hydrochloride (1:1)

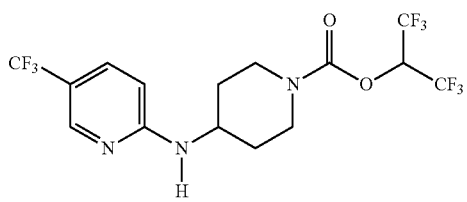 [SMILES: O=C(OC(C(F)(F)F)C(F)(F)F)N1CCC(Nc2ccc(C(F)(F)F)cn2)CC1]

6.1. tert-Butyl 4-(5-(trifluoromethyl)pyridin-2-ylamino)piperidine-1-carboxylate A mixture of 0.678 g (3 mmol) of 2-bromo-5-(trifluoromethyl)pyridine, 0.901 g (4.5 mmol) of tert-butyl 4-aminopiperidine-1-carboxylate and 0.829 g (6 mmol) of potassium carbonate in 5 ml of dimethyl sulphoxide is heated at 100° C. for 20 hours. The mixture is cooled to ambient temperature and then 50 ml of ethyl acetate and 15 ml of water are added. The organic phase is separated by settling and washed twice with 15 ml of water and then with 15 ml of a saturated aqueous sodium chloride solution. It is dried over sodium sulphate and evaporated under vacuum. The product is purified by chromatography on silica gel, elution being carried out with a 20:80 and then 30:70 mixture of ethyl acetate and cyclohexane in order to obtain 0.864 g (2.5 mmol) of product in the form of a white solid.

Melting point (° C.): 152

6.2. (Piperidin-4-yl)(5-(trifluoromethyl)pyridin-2-yl)amine 0.860 g (2.49 mmol) of tert-butyl 4-(5-(trifluoromethyl)(pyridin-2-ylamino)piperidine-1-carboxylate obtained in stage 6.1. is dissolved in 8.5 ml of dichloromethane. 1.91 ml of trifluoroacetic acid are added and the mixture is stirred at ambient temperature for 4 hours. The dichloromethane is evaporated and then the residue is coevaporated twice with 10 ml of 1,2-dichloroethane. The residue is taken up in a mixture of 50 ml of ethyl acetate, 10 ml of a 1N aqueous sodium hydroxide solution and 5 ml of a 33% aqueous ammonia solution. The organic phase is separated by settling. It is washed with 2 times 10 ml of water and then with 10 ml of a saturated aqueous sodium chloride solution. It is dried over sodium sulphate and evaporated to dryness to produce 0.572 g (2.33 mmol) of product in the form of an off-white solid.

Melting point (° C.): 128

6.3. 2,2,2-Trifluoro-1-(trifluoromethyl)ethyl 4-(5-(trifluoromethyl)(pyridin-2-ylamino)piperidine-1-carboxylate A solution of 0.467 g (2.32 mmol) of 4-nitrophenyl chloroformate in 3 ml of dichloromethane is added dropwise to a solution, cooled to 0° C., under an argon atmosphere, of 0.781 g (4.64 mmol) of 1,1,1,3,3,3-hexafluoro-2-propanol, 0.38 ml (4.64 mmol) of pyridine and 0.014 g (0.11 mmol) of 4-dimethylaminopyridine in 1.5 ml of dichloromethane. The mixture is left at ambient temperature overnight and then 0.569 g (2.32 mmol) of (piperidin-4-yl)(5-(trifluoromethyl)pyridin-2-yl)amine obtained in stage 6.2. and 1.22 ml (6.96 mmol) of diisopropylethylamine in 5 ml of dichloromethane are added. The mixture is stirred for 5 hours and then evaporated. The residue is taken up in a mixture of 10 ml of ethyl acetate, 50 ml of diethyl ether and 20 ml of water. The organic phase is separated by settling and then washed with 3 times 20 ml of a 1M aqueous potassium carbonate solution. The aqueous phases are reextracted with 20 ml of diethyl ether. The organic phases are washed with 20 ml of water and then 20 ml of a saturated aqueous sodium chloride solution. They are dried over sodium sulphate and evaporated to dryness. The product is purified by chromatography on silica gel, elution being carried out with a 15:85 and then 20:80 mixture of ethyl acetate and cyclohexane, in order to obtain 0.766 g (1.74 mmol) of product in the form of a white solid.

$^1$H NMR (CDCl$_3$, δ ppm, 200 MHz): 8.3 (s, 1H), 7.55 (d.d, 1H), 6.25 (d, 1H), 5.75 (sept., 1H), 4.7 (d, 1H), 4.1 (m, 3H), 3.15 (m, 2H), 2.15 (m, 2H), 1.45 (m, 2H).

6.4. 2,2,2-Trifluoro-1-(trifluoromethypethyl 4-(5-(trifluoromethyl)(pyridin-2-ylamino)piperidine-1-carboxylate hydrochloride (1:1)

0.75 g (1.71 mmol) of 2,2,2-trifluoro-1-(trifluoromethypethyl 4-(5-(trifluoromethyl)pyridin-2-ylamino)piperidine-1-carboxylate, obtained in stage 6.3, is dissolved in 15 ml of diisopropyl ether. 0.68 ml of a 5N solution of hydrochloric acid in isopropanol is added. The mixture is evaporated to dryness. The residue is recrystallized under hot conditions from a mixture of acetone and diisopropyl ether in order to obtain 0.616 g (1.30 mmol) of product in the form of white crystals.

Melting point (° C.): 225-235 (decomposition)
LC/MS (method B): Rt 9 min, m/z 440 (MH+)
IR (KBr, cm$^{-1}$): 1740, 1673, 1624
$^1$H NMR (CD$_3$OD, δ ppm, 400 MHz): 8.25 (s, 1H), 8.05 (d.d, 1H), 7.15 (d, 1H), 6.15 (sept., 1H), 4.2 (m, 2H), 4.0 (m, 1H), 3.2 (m, 2H), 2.1 (m, 2H), 1.6 (m, 2H).

Example 7

Compound No. 120

2,2,2-Trifluoro-1-(trifluoromethyl)ethyl 4-[(4-chlorobenzenesulphonylamino)methyl]-piperidine-1-carboxylate

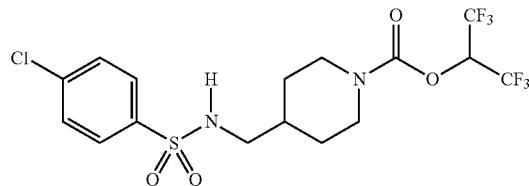 [SMILES: O=C(OC(C(F)(F)F)C(F)(F)F)N1CCC(CNS(=O)(=O)c2ccc(Cl)cc2)CC1]

7.1. tert-Butyl 4-[(4-chlorobenzenesulphonylamino)methyl]piperidine-1-carboxylate A solution of 0.844 g (4 mmol) of 4-chlorobenzenesulphonyl chloride in 5 ml of dichloromethane is added dropwise to a solution of 0.857 g (4 mmol) of tert-butyl 4-(aminomethyl) piperidine-1-carboxylate, 0.99 ml (6 mmol) of diisopropylethylamine and 0.024 g (0.2 mmol) of 4-dimethylaminopyridine in 9 ml of dichloromethane. The mixture is stirred at ambient temperature overnight. The organic phase is washed with 10 ml of water and then 4 ml of a 1N aqueous hydrochloric acid solution, 2 times 14 ml of water, 2 times 14 ml of a 1N aqueous sodium hydroxide solution, 3 times 14 ml of water and 14 ml of a saturated aqueous sodium chloride solution. It is dried over sodium sulphate and evaporated to dryness in order to obtain 1.371 g (3.52 mmol) of product in the form of an orange paste used as is in the following stage.

7.2. 4-Chloro-N-(piperidin-4-ylmethyl)benzenesulphonamide 1.364 g (3.51 mmol), tert-butyl 4-[(4-chlorobenzenesulphonylamino)methyl]piperidine-1-carboxylate, obtained in stage 7.1., are dissolved in 11 ml of dichloromethane. 2.7 ml (35 mmol) of trifluoroacetic acid are added. The mixture is stirred for 4 hours and then evaporated to dryness. The residue is taken up in 11 ml of a 1N aqueous hydrochloric acid solution. The aqueous phase is washed with 3 times 11 ml of diethyl ether and then 1.6 ml of a 33% aqueous sodium hydroxide solution are added. Extraction is carried out with 3 times 11 ml of dichloromethane and then with 3 times 15 ml of chloroform. The organic phases are dried over sodium sulphate and evaporated to dryness in order to obtain 0.847 g (2.93 mmol) of product in the form of a white solid.

7.3. 2,2,2-Trifluoro-1-(trifluoromethyl)ethyl 4-[(4-chlorobenzenesulphonylamino)methyl]-piperidine-1-carboxylate A solution of 0.59 g (2.93 mmol) of 4-nitrophenyl chloroformate in 6 ml of dichloromethane is added dropwise to a solution, cooled to 0° C., under an argon atmosphere, of 0.984 g (5.86 mmol) of 1,1,1,3,3,3-hexafluoro-2-propanol, 0.48 ml (5.86 mmol) of pyridine and 0.015 g (0.17 mmol) of 4-dimethylaminopyridine in 6 ml of dichloromethane. The mixture is left at ambient temperature overnight and then a mixture of 0.846 g (2.93 mmol) of 4-chloro-N-(piperidin-4-ylmethyl) benzenesulphonamide obtained in stage 7.2. and 1.21 ml (7.33 mmol) of diisopropylethylamine in 9 ml of dichloromethane is added. The mixture is stirred at ambient temperature for 5 hours and then evaporated to dryness. The residue is taken up in a mixture of 16 ml of ethyl acetate and 56 ml of diethyl ether. The organic phase is washed with 4 times 50 ml of water and then 70 ml of a 1M aqueous sodium carbonate solution, 70 ml of water and 70 ml of a saturated aqueous sodium chloride solution. It is dried over sodium sulphate and evaporated to dryness. The residue is purified by chromatography on silica gel, elution being carried out with a 25:75 mixture of ethyl acetate and cyclohexane. Crystallization is carried out from n-hexane in order to obtain 0.849 g (1.75 mmol) of product in the form of a white solid.

Melting point (° C.): 136-138
LC/MS (method C): Rt 6.4 min, m/z 483 (MH+)
IR (KBr, cm$^{-1}$): 3272, 1726

$^1$H NMR (CDCl$_3$, δ ppm, 400 MHz): 7.85 (d, 2H), 7.55 (d, 2H), 5.75 (sept., 1H), 4.50 (m, 1H), 4.20 (m, 2H), 2.90 (m, 4H), 1.75 (m, 3H), 1.15 (m, 2H).

Example 8

Compound No. 166

2,2,2-Trifluoro-1-(trifluoromethyl)ethyl 4-[3-(3-chlorophenyl)ureido]piperidine-1-carboxylate

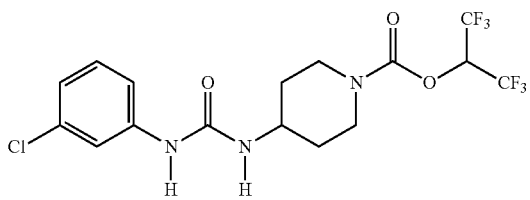 [SMILES: O=C(Nc1cccc(Cl)c1)NC1CCN(C(=O)OC(C(F)(F)F)C(F)(F)F)CC1]

8.1. 2,2,2-Trifluoro-1-(trifluoromethyl)ethyl 4-(tert-butoxycarbonylamino)piperidine-1-carboxylate A solution of 3.02 g (15 mmol) of 4-nitrophenyl chloroformate is added dropwise to a solution, cooled to 0° C., under an argon atmosphere, of 3.15 ml (30 mmol) of 1,1,1,3,3,3-hexafluoro-2-propanol, 2.42 ml (30 mmol) of pyridine and 0.091 g (0.75 mmol) of 4-dimethylaminopyridine in 10 ml of dichloromethane. The mixture is left to react at ambient temperature overnight. It is cooled to 0° C. and 3.00 g (15 mmol) of tert-butyl (piperidin-4-yl)carbamate are added portionwise and then 6.55 ml (37.5 mmol) of diisopropylethylamine are added dropwise. The mixture is stirred at ambient temperature for 5 hours and evaporated. The residue is taken up in a mixture of 20 ml of ethyl acetate, 30 ml of water and 60 ml of diethyl ether. The organic phase is separated by settling. It is washed with 30 ml of water and then with 4 times 30 ml of a 1M aqueous sodium carbonate solution, 2 times 30 ml of water and 30 ml of a saturated aqueous sodium chloride solution. It is dried over sodium sulphate and evaporated to dryness in order to obtain 5.18 g (13.1 mmol) of product in the form of an off-white solid.

Melting point (° C.): 104-106
IR (KBr, cm$^{-1}$): 1731, 1678

$^1$H NMR (CDCl$_3$, δ ppm, 200 MHz): 5.65 (sept., 1H), 4.3 (m, 1H), 4.0 (m, 2H), 3.6 (m, 1H), 2.95 (m, 2H), 1.95 (m, 2H), 1.4-1.2 (m+s, 11H).

8.2. 2,2,2-Trifluoro-1-(trifluoromethyl)ethyl 4-aminopiperidine-1-carboxylate hydrochloride 5.10 g (12.93 mmol) of 2,2,2-trifluoro-1-(trifluoromethyl)ethyl 4-(tert-butoxycarbonylamino)piperidine-1-carboxylate obtained in stage 8.1. are dissolved in 18 ml of dichloromethane, and 5.2 ml of a 5N solution of hydrochloric acid in isopropanol are added with stirring. After 3 hours, a further 2.6 ml of the hydrochloric acid solution are added. Stirring is continued at ambient temperature overnight. The mixture is evaporated to dryness. 50 ml of diisopropyl ether are added. Stirring is continued for 3 hours. The solid is filtered off and then dried under vacuum in the presence of phosphorus pentoxide in order to obtain 4.27 g (12.9 mmol) of product in the form of an off-white powder.

Melting point (° C.): 204-206
IR (KBr, cm$^{-1}$): 1731

$^1$H NMR (DMSO, δ ppm, 200 MHz): 8.2 (m, 3H), 6.6 (sept., 1H), 4.0 (m, 2H), 3.4-2.9 (m, 3H), 2.0 (m, 2H), 1.45 (m, 2H).

8.3. 2,2,2-Trifluoro-1-(trifluoromethypethyl 4-[3-(3-chlorophenyl)ureido]piperidine-1-carboxylate 0.30 ml (1.72 mmol) of diisopropylethylamine and then 0.230 g (1.5 mmol) of 3-chlorophenyl isocyanate in solution in 3 ml of dichloromethane are added to a suspension of 0.545 g (1.65 mmol) of 2,2,2-trifluoro-1-(trifluoromethyl)ethyl 4-aminopiperidine-1-carboxylate hydrochloride, obtained in stage 8.2., in 3 ml of dichloromethane. The mixture is stirred at ambient temperature overnight. It is evaporated to dryness. The residue is taken up in a mixture of 40 ml of ethyl acetate and 10 ml of water. The organic phase is separated by settling. It is washed with 10 ml of water and then 10 ml of a 1N aqueous hydrochloric acid solution, 10 ml of water and 10 ml of a saturated aqueous sodium chloride solution. It is dried over sodium sulphate and evaporated to dryness. The product is purified by chromatography on silica gel, elution being carried out with a 30:70 and then 40:60 mixture of ethyl acetate and cyclohexane. Recrystallization is carried out under hot conditions from a mixture of ethyl acetate and n-hexane in order to obtain 0.51 g (1.14 mmol) of product in the form of a white crystalline powder.

Melting point (° C.): 204-206
LC/MS (method D): Rt 1.27 min, m/z 448 (MH+)
IR (KBr, cm$^{-1}$): 1725, 1683
$^1$H NMR (DMSO, δ ppm, 400 MHz): 8.55 (s, 1H), 7.65 (s, 1H), 7.25 (m, 2H), 6.95 (d.d, 1H), 6.55 (sept., 1H), 6.35 (d, 1H), 3.9 (m, 2H), 3.75 (m, 1H), 3.2 (m, 2H), 1.9 (m, 2H), 1.35 (m, 2H).

Example 9

Compound No. 87

2,2,2-Trifluoro-1-(trifluoromethyl)ethyl 4-{[2-(4-chlorophenoxy)-2-methylpropionylamino]-methyl}piperidine-1-carboxylate

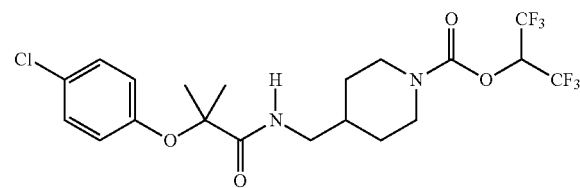 [SMILES: CC(C)(Oc1ccc(Cl)cc1)C(=O)NCC1CCN(C(=O)OC(C(F)(F)F)C(F)(F)F)CC1]

9.1. 2,2,2-Trifluoro-1-(trifluoromethyl)ethyl 4-(aminomethyl)piperidine-1-carboxylate hydrochloride As described in the preceding Examples 2, 6.3. and 7.3., a mixture of 0.41 ml (3.91 mmol) of 1,1,1,3,3,3-hexafluoro-2-propanol, 0.32 ml (3.91 mmol) of pyridine, 0.023 g (0.19 mmol) of 4-dimethylaminopyridine and 0.75 g (3.72 mmol) of 4-nitrophenyl chloroformate in solution in 13 ml of dichloromethane is left to react at ambient temperature overnight. 0.84 g (3.90 mmol) of tert-butyl (piperidin-4-yl)methylcarbamate and 2.1 ml (11.7 mmol) of diisopropylethylamine are added. The mixture is stirred at ambient temperature for 4 hours. The organic phase is washed with 5 times 25 ml of a 1N aqueous sodium hydroxide solution and then with 2 times 25 ml of a 1N aqueous hydrochloric acid solution. It is dried over magnesium sulphate in order to obtain 1.6 g of product in the form of an oil.

The product is taken up in 9.7 ml (39 mmol) of a 4N solution of hydrochloric acid in dioxane. The mixture is stirred at ambient temperature overnight and then evaporated to dryness. The residue is taken up in diethyl ether and the product is filtered off and dried under vacuum in order to obtain 0.91 g (2.64 mmol) of product in the form of an off-white powder.

Melting point (° C.): 177-178
IR (KBr, cm$^{-1}$): 1716
$^1$H NMR (DMSO, δ ppm, 200 MHz): 7.95 (m, 3H), 6.55 (sept., 1H), 4.0 (m, 2H), 3.0 (m, 2H), 2.75 (m, 2H), 1.85 (m, 3H), 1.15 (m, 2H).

9.2. 2,2,2-Trifluoro-1-(trifluoromethyl)ethyl 4-{[2-(4-chlorophenoxy)-2-methyl-propionylamino]methyl}piperidine-1-carboxylate 0.10 g (0.29 mmol) of 2,2,2-trifluoro-1-(trifluoromethyl) ethyl 4-(aminomethyl)piperidine-1-carboxylate hydrochloride, obtained in stage 9.1., and 0.071 g (0.29 mmol) of 2-(4-chlorophenoxy)-2-methylpropionyl chloride are dissolved in 1.5 ml of dichloromethane. 0.13 ml (0.73 mmol) of diisopropylethylamine is added. The mixture is stirred at ambient temperature overnight. 1.5 ml of dichloromethane are added. The organic phase is washed with 2 ml of a 1N aqueous hydrochloric acid solution, then filtered through a hydrophobic cartridge and evaporated to dryness. The product is purified by chromatography on silica gel, elution being carried out with a gradient of 10:90 to 40:60 of ethyl acetate and cyclohexane, in 15 min, in order to obtain 0.089 g (0.176 mmol) of product in the form of a white powder.

Melting point (° C.): 77-78
LC/MS (method D): Rt 1.44 min, m/z 505 (MH+)
IR (KBr, cm$^{-1}$): 1749, 1655
$^1$H NMR (DMSO, δ ppm, 400 MHz): 8.2 (t, 1H), 7.35 (d, 2H), 6.9 (d, 2H), 6.55 (sept., 1H), 3.9 (m, 2H), 3.0-2.85 (m, 4H), 1.7 (m, 1H), 1.55 (d, 2H), 1.45 (s, 6H), 1.0 (m, 2H).

Example 10

Compound No. 191

2,2,2-Trifluoro-1-(trifluoromethyl)ethyl 3-[2-(3-methyl-3-phenylureido)ethyl]azetidine-1-carboxylate

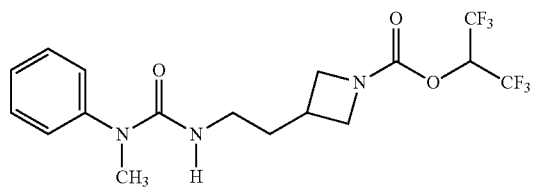 [SMILES: CN(C(=O)NCCC1CN(C(=O)OC(C(F)(F)F)C(F)(F)F)C1)c1ccccc1]

10.1. 2,2,2-Trifluoro-1-(trifluoromethypethyl 3-(2-aminoethyl)azetidine-1-carboxylate hydrochloride As described in the preceding Example 9.1., a mixture of 1.65 ml (15.63 mmol) of 1,1,1,3,3,3-hexafluoro-2-propanol, 1.27 ml (15.63 mmol) of pyridine, 0.090 g (0.74 mmol) of 4-dimethylaminopyridine and 3.0 g (14.88 mmol) of 4-nitrophenyl chloroformate in solution in 50 ml of dichloromethane is left to react at ambient temperature overnight. Half the solution is withdrawn. 1.853 g (7.83 mmol) of tert-butyl (2-(azetidin-3-yl)ethyl)carbamate, 4.19 ml (23.49 mmol) of diisopropylethylamine and 20 ml of dichloromethane are added. The mixture is stirred at ambient temperature overnight. The organic phase is subsequently washed with 3 times 50 ml of a 1N aqueous sodium hydroxide solution and then with 50 ml of a 1N aqueous hydrochloric acid solution. It is dried over magnesium sulphate and evaporated to dryness in order to obtain 3.00 g of product.

The product is taken up in 19 ml (76 mmol) of a 4N solution of hydrochloric acid in dioxane. A further 20 ml of dioxane are added. The mixture is stirred at ambient temperature for 5 hours. It is evaporated to dryness in order to obtain 2.50 g (7.56 mmol) of product in the form of an oil which solidifies.

Melting point (° C.): 116-117
IR (KBr, cm$^{-1}$): 1731
$^1$H NMR (DMSO, δ ppm, 200 MHz): 8.0 (m, 3H), 6.5 (sept., 1H), 4.15 (m, 2H), 3.75 (m, 2H), 2.75 (m, 3H), 1.9 (m, 2H).

10.2. 2,2,2-Trifluoro-1-(trifluoromethypethyl 3-[2-(3-methyl-3-phenylureido)ethyl]azetidine-1-carboxylate 0.112 g (0.34 mmol) of 2,2,2-trifluoro-1-(trifluoromethypethyl 3-(2-aminoethyl)azetidine-1-carboxylate hydrochloride, obtained in stage 10.1., is dissolved in 2 ml of dichloromethane. 0.054 g (0.32 mmol) of N-methyl-N-phenylcarbamoyl chloride and 0.15 ml (0.85 mmol) of diisopropylethylamine are added. The mixture is stirred at ambient temperature overnight. The organic phase is washed with 3 times 2 ml of a 1N aqueous sodium hydroxide solution and then with 2 ml of a 1N aqueous hydrochloric acid solution.

It is dried by filtration through a hydrophobic cartridge and evaporated to dryness. The product is purified by chromatography on silica gel, elution being carried out with a gradient of 15:85 to 45:55 ethyl acetate and cyclohexane, in 15 minutes, in order to obtain 0.06 g (0.14 mmol) of product in the form of a white powder.

Melting point (° C.): 101-102
LC/MS (method D): Rt 1.2 min, m/z 428 (MH+)
IR (KBr, cm$^{-1}$): 3353, 1738, 1643
$^1$H NMR (DMSO, δ ppm, 400 MHz): 7.4 (m, 2H), 7.25 (m, 3H), 6.45 (sept., 1H), 6.0 (t, 1H), 4.1 (m, 2H), 3.75 (m, 2H), 3.15 (s, 3H), 3.0 (m, 2H), 2.65 (m, 1H), 1.7 (m, 2H).

Example 11

Compound No. 113

2,2,2-Trifluoro-1-(trifluoromethyl)ethyl 3-[(naphthalene-1-sulphonylamino)methyl]-pyrrolidin e-1-carboxylate

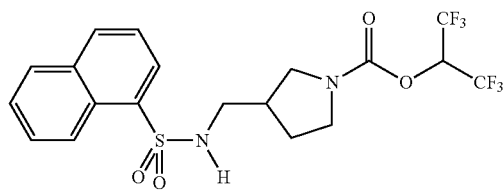 [SMILES: O=C(OC(C(F)(F)F)C(F)(F)F)N1CCC(CNS(=O)(=O)c2cccc3ccccc23)C1]

11.1. 2,2,2-Trifluoro-1-(trifluoromethypethyl 3-(aminomethyl)pyrrolidine-1-carboxylate hydrochloride The procedure is the same as described in Example 10.1. using 1.56 g (7.83 mmol) of tert-butyl (pyrrolidin-3-ylmethyl)carbamate (in place of tert-butyl (2-(azetidin-3-yl)ethyl)carbamate), in order to obtain 1.51 g (4.56 mmol) of product in the form of an oil, used as is in the following stage. A solid sample is obtained by triturating from ethyl acetate.

Melting point (° C.): 190° C. (decomposition)
IR (KBr, cm$^{-1}$): 1732
$^1$H NMR (DMSO, δ ppm, 200 MHz): 7.90 (m, 3H), 6.55 (sept., 1H), 3.65 (m, 1H), 3.55 (m, 1H), 3.40 (m, 1H), 3.15 (m, 1H), 2.95 (m, 2H), 2.50 (m, 1H), 2.10 (m, 1H), 1.75 (m, 1H).

11.2. 2,2,2-Trifluoro-1-(trifluoromethyl)ethyl 3-[(naphthalene-1-sulphonylamino)methyl]-pyrrolidin e-1-carboxylate The procedure is the same as described in Example 10.2. using 0.10 g (0.30 mmol) of 2,2,2-trifluoro-1-(trifluoromethyl)ethyl 3-(aminomethyl)pyrrolidine-1-carboxylate hydrochloride obtained in stage 11.2., 0.066 g (0.29 mmol) of naphthalene-1-sulphonyl chloride and 0.13 ml (0.76 mmol) of diisopropylethylamine, in order to obtain, after purification by chromatography on silica gel, 0.096 g (0.20 mmol) of product in the form of a white powder.

Melting point (° C.): 135-136
LC/MS (method C): Rt 4.88 min, m/z 485 (MH+)
IR (KBr, cm$^{-1}$): 1732
$^1$H NMR (DMSO, δ ppm, 400 MHz): 8.65 (d, 1H), 8.25 (d, 1H), 8.15 (m, 3H), 7.75-7.60 (m, 3H), 6.45 (sept., 1H), 3.45-3.20 (m, 3H), 3.05 (m, 1H), 2.85 (m, 2H), 2.30 (m, 1H), 1.85 (m, 1H), 1.55 (m, 1H).

Example 12

Compound No. 220

2,2,2-Trifluoro-1-(trifluoromethyl)ethyl 3-[1-(4-chlorobenzenesulphonylamino)cyclopropyl]-azetidine-1-carboxylate

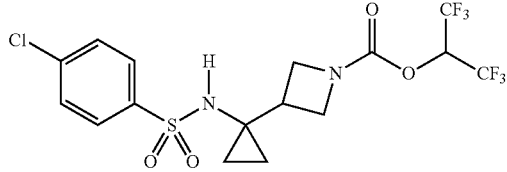 [SMILES: O=C(OC(C(F)(F)F)C(F)(F)F)N1CC(C2(NS(=O)(=O)c3ccc(Cl)cc3)CC2)C1]

12.1. tert-Butyl 3-(1-aminocyclopropyl)azetidine-1-carboxylate 10.5 ml (35 mmol) of titanium tetraisopropoxide (Ti(OiPr)$_4$) and then, dropwise, 21 ml (63 mmol) of a 3M solution of ethylmagnesium bromide in diethyl ether are added, under a nitrogen atmosphere, to a solution of 4.8 g (26.34 mmol) of tert-butyl 4-cyanoazetidine-1-carboxylate in 150 ml of diethyl ether. The mixture is stirred for 40 minutes and then 9 ml (71 mmol) of the boron trifluoride etherate complex (BF$_3$.Et$_2$O) are added dropwise. The reaction mixture is stirred for 5 hours. 100 ml of a 2M aqueous sodium hydroxide solution and 150 ml of dichloromethane are added. The mixture is filtered through celite. The organic phase is separated by settling. It is dried over sodium sulphate and evaporated to dryness. The product is purified by chromatography on silica gel, elution being carried out with a 90:10 mixture of dichloromethane and methanol, in order to obtain 1.91 g (9.0 mmol) of product in the form of a colourless oil which slowly solidifies.

$^1$H NMR (CDCl$_3$, δ ppm, 200 MHz): 3.65 (t, 2H), 3.35 (m, 2H), 2.30-2.20 (m, 1H), 1.45 (s, 2H), 1.15 (s, 9H), 0.35 (m, 2H), 0.20 (m, 2H).

12.2. tert-Butyl 3-[1-(4-chlorobenzenesulphonylamino)cyclopropyl]azetidine-1-carboxylate 0.35 g (1.65 mmol) of tert-butyl 3-(1-aminocyclopropyl)azetidine-1-carboxylate, obtained in stage 12.1., 0.6 ml (3.44 mmol) of diisopropylethylamine and 0.34 g (1.61 mmol) of 4-chlorobenzenesulphonyl chloride are dissolved in 4 ml of dichloromethane. The mixture is stirred at ambient temperature for 20 hours. 20 ml of dichloromethane are added and washing is carried out with 10 ml of a 1N aqueous hydrochloric acid solution, then 10 ml of a 1N aqueous sodium hydroxide solution and 10 ml of a saturated aqueous sodium chloride solution. The organic phase is filtered through a hydrophobic cartridge and evaporated to dryness. The residue is purified by chromatography on silica gel, elution being carried out with a 95:5 mixture of dichloromethane and methanol, in order to obtain 0.30 g (0.77 mmol) of product in the form of a white solid.

$^1$H NMR (CDCl$_3$, δ ppm, 200 MHz): 7.85 (m, 2H), 7.55 (m, 2H), 5.55 (s, 1H), 3.90 (t, 2H), 3.50 (m, 2H), 3.15-3.00 (m, 1H), 1.50 (s, 9H), 0.80 (s, 4H).

12.3. N-(1-(Azetidin-3-yl)cyclopropyl)-4-chlorobenzenesulphonamide hydrochloride 0.30 g (0.78 mmol) of tert-butyl 3-[1-(4-chlorobenzenesulphonylamino)cyclopropyl]-azetidine-1-carboxylate, obtained in stage 12.2., is dissolved in 10 ml of methanol. 0.2 ml (1.58 mmol) of trimethylsilyl chloride is added. The mixture is stirred at ambient temperature overnight. A further 0.2 ml of trimethylsilyl chloride is added and stirring is continued for 4 hours. The mixture is concentrated under vacuum and then the residue is taken up in ethyl acetate and evaporated to dryness in order to obtain 0.28 g of product in the form of a white solid used as is.

12.4. 2,2,2-Trifluoro-1-(trifluoromethypethyl 3-[1-(4-chlorobenzenesulphonylamino)cyclo-propyl]azetidine-1-carboxylate A solution of 2.0 g (9.9 mmol) of 4-nitrophenyl chloroformate in 10 ml of dichloromethane is added dropwise to a solution of 2.50 g (14.9 mmol) of 1,1,1,3,3,3-hexafluoro-2-propanol and 1.90 ml (23.5 mmol) of pyridine in 40 ml of dichloromethane. The mixture is left to react at ambient temperature overnight.

5 ml of this solution are withdrawn and 0.28 g (0.87 mmol) of N-(1-azetidin-3-yl-cyclopropyl)-4-chlorobenzenesulphonamide hydrochloride, obtained in stage 12.3., and 1.3 ml (7.46 mmol) of diisopropylethylamine are added. The mixture is stirred for 8 hours. Washing is carried out with 2 times 10 ml of a 0.5N aqueous hydrochloric acid solution and then 3 times 10 ml of a saturated aqueous sodium carbonate solution. The organic phase is filtered through a hydrophobic cartridge and evaporated to dryness. The residue is purified by chromatography on silica gel, elution being carried out with a 95:5 mixture of dichloromethane and methanol, in order to obtain 0.32 g (0.66 mmol) of product in the form of a white powder.

Melting point (° C.): 108-109

LC/MS (method C): Rt 4.97 min, m/z 481 (MH+)

IR (KBr, cm$^{-1}$): 1761, 1736

$^1$H NMR (DMSO, δ ppm, 400 MHz): 8.55 (s, 1H), 7.80 (d, 2H), 7.70 (d, 2H), 6.45 (septet, 1H), 3.90 (m, 2H), 3.70 (m, 2H), 2.85 (m, 1H), 0.65 (m, 2H), 0.60 (m, 2H).

Example 13

Compound No. 231

2,2,2-Trifluoro-1-(trifluoromethyl)ethyl 4-(4-carbamoylpyrazol-1-ylmethyl)piperidine-1-carboxylate

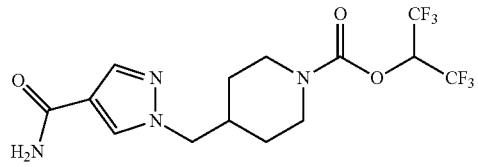 [SMILES: NC(=O)c1cnn(CC2CCN(C(=O)OC(C(F)(F)F)C(F)(F)F)CC2)c1]

13.1. tert-Butyl 4-(4-carbamoylpyrazol-1-ylmethyl)piperidine-1-carboxylate 2.15 g (10 mmol) of tert-butyl 4-(hydroxymethyl)piperidine-1-carboxylate, 2.11 ml (15 mmol) of triethylamine and 0.06 g (0.5 mmol) of 4-dimethylaminopyridine are dissolved in 15 ml of dichloromethane under an argon atmosphere. The solution is cooled with an ice bath and a solution of 1.60 g (14 mmol) of methanesulphonyl chloride in 5 ml of dichloromethane is added dropwise. The mixture is stirred at the temperature of the ice bath for one hour and then at ambient temperature for 2 hours. 20 ml of water and 20 ml of dichloromethane are added. The organic phase is separated by settling and washed with 20 ml of a 0.5N aqueous hydrochloric acid solution, then twice with 20 ml of water and 20 ml of a saturated aqueous sodium chloride solution. The organic phase is dried over sodium sulphate and evaporated to dryness in order to obtain 2.96 g (10 mmol) of mesylate in the form of an orange oil.

1.76 g (6 mmol) of this product are redissolved in 6 ml of N,N-dimethylformamide. 0.76 g (6.9 mmol) of 1H-pyrazole-4-carboxamide and 1.24 g (9 mmol) of potassium carbonate are added with stirring and the mixture is heated at 70° C. overnight. 30 ml of ethyl acetate are added and the solid is filtered off and washed with 6 ml of a 1:5 mixture of N,N-dimethylformamide and ethyl acetate and then 6 ml of ethyl acetate. The filtrates are evaporated to dryness. The residue is taken up in 50 ml of a 95:5 mixture of chloroform and methanol. The insoluble material is filtered off and washed twice with a 95:5 mixture of chloroform and methanol. The filtrates are evaporated to dryness and the residue is recrystallized under hot conditions from ethyl acetate in order to obtain 0.98 g (3.17 mmol) of product in the form of a white powder.

Melting point (° C.): 190-192

$^1$H NMR (CDCl$_3$, δ ppm, 200 MHz): 7.80 (s, 1H), 7.70 (s, 1H), 5.55 (m, 2H), 4.05 (broad d, 2H), 3.95 (d, 2H), 2.60 (t, 2H), 2.00 (m, 1H), 1.45 (broad d, 2H), 1.80 (s, 9H), 1.20-1.00 (m, 2H).

13.2. 1-(Piperidin-4-ylmethyl)-1H-pyrazole-4-carboxamide hydrochloride

A suspension of 0.96 g (3.11 mmol) of tert-butyl 4-(4-carbamoylpyrazol-1-ylmethyl)piperidine-1-carboxylate, obtained in stage 13.1., in 25 ml of a 5N solution of hydrochloric acid (124 mmol) in isopropanol is stirred overnight. It is evaporated to dryness and then coevaporated twice with 25 ml of ethyl acetate. The product is resuspended in 25 ml of ethyl acetate. It is filtered, washed twice with 10 ml of ethyl acetate and dried under vacuum in order to obtain 0.91 g (3.23 mmol) of product in the form of a white powder.

¹H NMR (DMSO+D₂O, δ ppm, 200 MHz): 8.15 (s, 1H), 7.85 (s, 1H), 4.05 (d, 2H), 3.25 (broad d, 2H), 2.80 (broad t, 2H), 2.10 (m, 1H), 1.60 (broad d, 2H), 1.45-1.25 (m, 2H).

13.3. 2,2,2-Trifluoro-1-(trifluoromethypethyl 4-(4-carbamoylpyrazol-1-ylmethyl)piperidine-1-carboxylate A solution of 0.605 g (3 mmol) of 4-nitrophenyl chloroformate in 5 ml of dichloromethane is added dropwise to a solution of 1.00 g (6 mmol) of 1,1,1,3,3,3-hexafluoro-2-propanol, 0.49 ml (6 mmol) of pyridine and 0.036 g (0.3 mmol) of 4-dimethylaminopyridine in 5 ml of dichloromethane. The mixture is left to react at ambient temperature overnight.

This solution is added dropwise, under an argon atmosphere, to a solution, cooled with an ice bath, of 0.84 g (3 mmol) of 1-(piperidin-4-ylmethyl)-1H-pyrazole-4-carboxamide hydrochloride, obtained in stage 13.2., and 2.2 ml (13 mmol) of diisopropylethylamine in a mixture of 15 ml of N,N-dimethylformamide and 7 ml of dimethyl sulphoxide. The reaction mixture is subsequently stirred at ambient temperature for 2 hours and evaporated under vacuum. The residue is taken up in 50 ml of ethyl acetate and 2.8 g (20 mmol) of potassium carbonate are added thereto. The mixture is stirred vigorously for 2 hours. The solid is filtered off and washed twice with 25 ml of ethyl acetate. The filtrate is subsequently washed twice with 10 ml of a semisaturated aqueous sodium chloride solution and then twice with 10 ml of a saturated aqueous sodium chloride solution. The filtrate is dried over sodium sulphate and evaporated to dryness. The product is purified by chromatography on silica gel, elution being carried out with a 97:3, then 95:5 and 92:8 mixture of dichloromethane and methanol, in order to obtain 1.0 g of product in the form of a white solid, contaminated by approximately 3 mol % of 4-nitro-phenyl 4-(4-carbamoylpyrazol-1-ylmethyl)piperidine-1-carboxylate.

0.80 g of this product is redissolved in 15 ml of ethyl acetate. 0.2 g of 10% palladium-on-charcoal is added thereto and the mixture is stirred under a hydrogen atmosphere of 2 bar for 3 hours. It is subsequently filtered through celite. Rinsing is carried out 4 times with 10 ml of ethyl acetate and the filtrate is evaporated to dryness. The product is purified by chromatography on silica gel, elution being carried out with a 97:3, then 95:5 and then 92:8 mixture of dichloromethane and methanol, in order to obtain 0.75 g of product in the form of a white solid. Recrystallization is carried out under hot conditions from a mixture of ethyl acetate and diisopropyl ether in order to obtain 0.68 g (1.69 mmol) of product in the form of a white powder.

Melting point (° C.): 98-118

LC/MS (method D): Rt 0.97 min, m/z 403 (MH+)

IR (KBr, cm⁻¹): 1722, 1656

¹H NMR (CDCl₃, δ ppm, 400 MHz): 7.90 (s, 1H), 7.80 (s, 1H), 5.75 (septet 1H), 5.55 (m, 2H), 4.20 (broad t, 2H), 4.05 (d, 2H), 2.90 (m, 2H), 2.20 (m, 1H), 1.65 (m, 2H), 1.25 (m, 2H).

Example 14

Compound No. 234

2,2,2-Trifluoro-1-(trifluoromethyl)ethyl 4-[2-(5-carbamoylpyrazin-2-ylamino)ethyl]piperidine-1-carboxylate

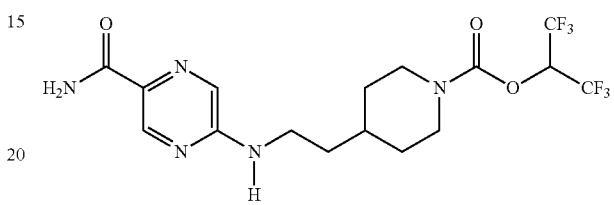

14.1. tert-Butyl 4-[2-(5-carbamoylpyrazin-2-ylamino)ethyl]piperidine-1-carboxylate A mixture of 1.12 g (7.15 mmol) of 5-chloropyrazine-2-carboxamide, 1.95 g (8.58 mmol) of tert-butyl 4-(2-aminoethyl)piperidine-1-carboxylate and 1.18 g (8.58 mmol) of potassium carbonate in 1.4 ml of dimethyl sulphoxide is heated during 5 hours at 100° C. under an argon atmosphere and with stirring. After cooling to ambient temperature, 25 ml of ethyl acetate and 25 ml of water are added. The organic phase is separated by settling and washed 3 times with 25 ml of water and then 25 ml of a saturated aqueous sodium chloride solution. It is dried over sodium sulphate and evaporated to dryness. The residue is purified by chromatography on silica gel, elution being carried out with a 97:3, then 95:5 and 93:7 mixture of dichloromethane and methanol, in order to obtain 1.99 g (5.69 mmol) of product in the form of a light-yellow paste.

¹H NMR (CDCl₃, δ ppm, 200 MHz): 8.65 (s, 1H), 8.10 (s, 1H), 7.55 (m, 1H), 5.75 (m, 1H), 4.85 (m, 1H), 4.15 (m, 2H), 3.45 (m, 2H), 2.75 (t, 2H), 1.80-1.60 (m, 5H), 1.50 (s, 9H), 1.35-1.10 (m, 2H).

14.2. 5-(2-(Piperidin-4-yl)ethylamino)pyrazine-2-carboxamide dihydrochloride 1.98 g (5.68 mmol) of tert-butyl 4-[2-(5-carbamoylpyrazin-2-ylamino)ethyl]piperidine-1-carboxylate, obtained in stage 14.1., are dissolved in 20 ml of dichloromethane. 13 ml of a 5N solution of hydrochloric acid in isopropanol are added and the mixture is stirred overnight. It is evaporated to dryness and then coevaporated twice with 50 ml of ethyl acetate. The residue is taken up in 17 ml of ethyl acetate and stirred for one hour. The solid is filtered off, washed with 2 times 5 ml of ethyl acetate and dried under vacuum in order to obtain 1.78 g (5.54 mmol) of product in the form of a yellow solid.

¹H NMR (DMSO+D₂O, δ ppm, 200 MHz): 8.20 (s, 1H), 8.10 (s, 1H), 3.40 (t, 2H), 3.25 (broad d, 2H), 2.80 (t, 2H), 1.90 (broad d, 2H), 1.70-1.15 (m, 5H).

14.3. 2,2,2-Trifluoro-1-(trifluoromethypethyl 4-[2-(5-carbamoylpyrazin-2-ylamino)ethyl]piperidine-1-carboxylate A solution of 1.01 g (5 mmol) of 4-nitrophenyl chloroformate in 8.5 ml of dichloromethane is added dropwise to a solution, cooled under argon with an ice bath, of 1.69 g (10 mmol) of 1,1,1,3,3,3-hexafluoro-2-propanol, 0.82 ml (10 mmol) of pyridine and 0.030 g (0.25 mmol) of 4-dimethylaminopyridine in 8.5 ml of dichloromethane. The mixture is left to react at ambient temperature overnight.

This solution is added dropwise, under an argon atmosphere and with stirring, to a mixture, cooled with a bath of cold water, of 1.62 g (5.04 mmol) of 5-(2-(piperidin-4-yl)ethylamino)pyrazine-2-carboxamide dihydrochloride, obtained in stage 14.2., and 3.75 ml (22 mmol) of diisopropylethylamine in 11 ml of dimethyl sulphoxide. The reaction mixture is subsequently stirred at ambient temperature for 4 hours and evaporated under vacuum. The residue is taken up in 110 ml of ethyl acetate and 4.7 g (34 mmol) of potassium carbonate are added thereto. The mixture is stirred vigorously for 4 hours. The solid is filtered off and washed twice with 30 ml of ethyl acetate. The filtrate is subsequently washed 3 times with 16 ml of a semisaturated aqueous sodium chloride solution and then 3 times with 16 ml of a saturated aqueous sodium chloride solution. The filtrate is dried over sodium sulphate and evaporated to dryness. The product is purified by chromatography on silica gel, elution being carried out with a 90:10 mixture of ethyl acetate and cyclohexane and then with ethyl acetate, in order to obtain 1.6 g of product. It is redissolved in 90 ml of ethyl acetate and washed 3 times with 7.5 ml of a 1M aqueous potassium carbonate solution and then twice with 7.5 ml of water. The organic phase is dried over sodium sulphate and evaporated in order to obtain 1.57 g of product. Recrystallization is carried out under hot conditions from a mixture of ethyl acetate and diisopropyl ether, in order to obtain 1.31 g (2.95 mmol) of product in the form of a light-yellow powder.

Melting point (° C.): 156-158

LC/MS (method D): Rt 1.16 min, m/z 444 (MH+)

IR (KBr, cm$^{-1}$): 1725, 1675

$^1$H NMR (DMSO, δ ppm, 400 MHz): 8.65 (s, 1H), 8.10 (s, 1H), 7.45 (broad s, 1H), 5.75 (septet, 1H), 5.55 (broad s, 1H), 4.70 (broad s, 1H), 4.15 (broad t, 2H), 3.50 (broad s, 2H), 2.90 (m, 2H), 1.80-1.20 (m, 7H).

The chemical structures and the physical properties of a few examples of compounds according to the invention are illustrated in the following Table 1. In this table:

M.p. (° C.) represents the melting point of the compound in degrees Celsius;

(m/z) represents the molecular ion observed in mass spectrometry (LC/MS);

(MH+) represents a molecular ion with protonation;

((M−H)—) represents a molecular ion with loss of a proton;

(M+) represents a molecular ion with loss of an electron;

(MH+ACN) represents a molecular ion in the form of an adduct with acetonitrile;

(MNH$_4$+) represents a molecular ion in the form of an adduct with ammonia;

(MACO$_2$—) represents a molecular ion in the form of an adduct with the acetate ion;

in the "Z" and "A" columns, "-" means that Z and/or A are absent;

in the "Salt" column, "-" represents a compound in the form of the free base and "HCl" represents a compound in the hydrochloride form;

"NC" represents a cyano group;

"-(c-prop)" represents a cyclopropylenyl group;

"—NHC-(c-prop)-" represents a group:

The compounds described in Table 1 were prepared according to the methods described above.

The retention times (Rt) of several compounds of Table 1, measured by LC/MS analysis according to one of the methods A, B, C, D or E described above, are illustrated in Table 2.

The optical rotations ([α]$_D$) obtained for the enantiomeric compounds 22, 23, 24 and 25 of Table 1 and the conditions for measuring [α]$_D$ are given in Table 3.

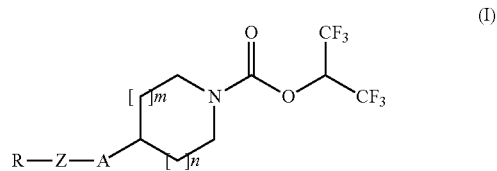

TABLE 1

| No. | R | Z | A | m | n | Salt | M.p. (° C.) | LC/MS (m/z) |
|---|---|---|---|---|---|---|---|---|
| 1. | 4-Cl-phenyl | — | — | 1 | 1 | — | 60-62 | 390 (MH+) |
| 2. | 3-CH$_3$-phenyl | — | — | 1 | 1 | oil | — | 411 (MH + ACN) |
| 3. | 2-CF$_3$-phenyl | — | — | 1 | 1 | oil | — | 465 (MH + ACN) |
| 4. | 2-CH$_3$O-phenyl | — | — | 1 | 1 | oil | — | 427 (MH + ACN) |
| 5. | 4-NC-phenyl | — | — | 1 | 1 | — | 54-56 | 398 (MNH$_4$+) |
| 6. | 4-CH$_3$NHCO-phenyl | — | — | 1 | 1 | oil | — | 413 (MH+) |
| 7. | naphth-1-yl | — | — | 1 | 1 | oil | — | 447 (MH + ACN) |
| 8. | benzoxazol-2-yl | — | — | 1 | 1 | — | 71-73 | 397 (MH+) |
| 9. | 5-F-benz[d]isoxazol-3-yl | — | — | 1 | 1 | — | 127-129 | 415 (MH+) |
| 10. | 6-F-benz[d]isoxazol-3-yl | — | — | 1 | 1 | — | 91-93 | 415 (MH+) |
| 11. | 2-oxobenzimidazol-1-yl | — | — | 1 | 1 | — | 196-198 | 412 (MH+) |
| 12. | 5-Cl-2-oxobenzimidazol-1-yl | — | — | 1 | 1 | — | 231-233 | 446 (MH+) |
| 13. | 5-CF$_3$-benzotriazol-1-yl | — | — | 1 | 1 | — | 127-129 | 465 (MH+) |
| 14. | 5-(4-F-phenyl)-1,3,4-oxadiazol-2-yl | — | — | 1 | 1 | — | 113-115 | 442 (MH+) |
| 15. | 6-F-indazol-3-yl | — | — | 1 | 1 | — | 137-141 | 414 (MH+) |
| 16. | phenyl | CH$_2$ | — | 1 | 1 | oil | — | 411 (MH + ACN) |
| 17. | 3-(4-Cl-phenyl)isoxazol-5-yl | CH$_2$ | — | 1 | 1 | — | 91-93 | 471 (MH+) |
| 18. | 4-Cl-phenyl | (CH$_2$)$_2$ | — | 1 | 1 | oil | — | 435 (MNH$_4$+) |
| 19. | 4-Cl-phenyl | C≡C | — | 1 | 1 | oil | — | 414 (MH+) |
| 20. | 3-(4-F-phenyl)phenyl | — | O | 0 | 0 | — | 68-69 | 438 (MH+) |
| 21. | 3-(3-NC-phenyl)phenyl | — | O | 0 | 0 | oil | — | 444 (M+) |

TABLE 1-continued

| No. | R | Z | A | m | n | Salt | M.p. (° C.) | LC/MS (m/z) |
|---|---|---|---|---|---|---|---|---|
| 22. | 3-(4-F-phenyl)phenyl | — | O | 0 | 1 | — | 72-73 | 452 (MH+) |
| 23. | 3-(4-F-phenyl)phenyl | — | O | 0 | 1 | — | 72-73 | 452 (MH+) |
| 24. | 3-(3-NC-phenyl)phenyl | — | O | 0 | 1 | oil | — | 476 (MNH$_4$+) |
| 25. | 3-(3-NC-phenyl)phenyl | — | O | 0 | 1 | oil | — | 476 (MNH$_4$+) |
| 26. | 4-F-phenyl | — | O | 1 | 1 | oil | — | 389 ((M − H)−) |
| 27. | 3-H$_2$NCO-phenyl | — | O | 1 | 1 | — | 121-123 | 415 (MH+) |
| 28. | 4-H$_2$NCO-phenyl | — | O | 1 | 1 | — | 153-155 | 415 (MH+) |
| 29. | 3-(3-F-phenyl)phenyl | — | O | 1 | 1 | oil | — | 466 (MH+) |
| 30. | 3-(4-F-phenyl)phenyl | — | O | 1 | 1 | — | 78-80 | 466 (MH+) |
| 31. | 3-(3-Cl-phenyl)phenyl | — | O | 1 | 1 | — | 70-72 | 482 (MH+) |
| 32. | 3-(4-Cl-phenyl)phenyl | — | O | 1 | 1 | — | 98-100 | 482 (MH+) |
| 33. | 3-(3-NC-phenyl)phenyl | — | O | 1 | 1 | — | 80-82 | 473 (MH+) |
| 34. | 3-(4-NC-phenyl)phenyl | — | O | 1 | 1 | — | 73-77 | 473 (MH+) |
| 35. | 4-(3-NC-phenyl)phenyl | — | O | 1 | 1 | — | 87-89 | 473 (MH+) |
| 36. | 4-(4-NC-phenyl)phenyl | — | O | 1 | 1 | — | 141-143 | 473 (MH+) |
| 37. | 3-(3-CH$_3$O-phenyl)phenyl | — | O | 1 | 1 | oil | — | 478 (MH+) |
| 38. | 3-(4-CH$_3$O-phenyl)phenyl | — | O | 1 | 1 | oil | — | 478 (MH+) |
| 39. | 4-Cl-naphth-1-yl | — | O | 1 | 1 | — | 88-90 | 514 (MACO$_2$−) |
| 40. | naphth-2-yl | — | O | 1 | 1 | — | 113-115 | 422 (MH+) |
| 41. | 6-NC-naphth-2-yl | — | O | 1 | 1 | — | 127-129 | 447 (MH+) |
| 42. | 6-CH$_3$O-naphth-2-yl | — | O | 1 | 1 | — | 120-122 | 452 (MH+) |
| 43. | 7-CH$_3$O-naphth-2-yl | — | O | 1 | 1 | — | 98-100 | 452 (MH+) |
| 44. | pyridin-4-yl | — | O | 1 | 1 | oil | — | 373 (MH+) |
| 45. | 6-(3-NC-phenyl)pyridin-2-yl | — | O | 1 | 1 | — | 124-126 | 474 (MH+) |
| 46. | 5-(3-NC-phenyl)pyridin-3-yl | — | O | 1 | 1 | — | 138-140 | 474 (MH+) |
| 47. | 6-(3-NC-phenyl)pyrimidin-4-yl | — | O | 1 | 1 | — | 129-133 | 475 (MH+) |
| 48. | 6-(4-F-phenyl)pyrazin-2-yl | — | O | 1 | 1 | — | 107-109 | 468 (MH+) |
| 49. | 6-(3-NC-phenyl)pyrazin-2-yl | — | O | 1 | 1 | — | 122-124 | 475 (MH+) |
| 50. | 3-H$_2$NCO-phenyl | — | OCH$_2$ | 1 | 1 | — | 109-111 | 429 (MH+) |
| 51. | 4-Cl-naphth-1-yl | — | OCH$_2$ | 1 | 1 | — | 141-143 | 470 (MH+) |
| 52. | 3-(4-NC-phenyl)phenyl | — | OCH$_2$ | 1 | 1 | — | 83-85 | 487 (MH+) |
| 53. | 3-(4-NC-phenyl)phenyl | — | OCH$_2$ | 1 | 1 | — | 109-111 | 487 (MH+) |
| 54. | 4-(3-NC-phenyl)phenyl | — | OCH$_2$ | 1 | 1 | — | 109-111 | 487 (MH+) |
| 55. | 4-(4-NC-phenyl)phenyl | — | OCH$_2$ | 1 | 1 | — | 133-135 | 487 (MH+) |
| 56. | naphth-2-yl | — | OCH$_2$ | 1 | 1 | — | 71-73 | 436 (MH+) |
| 57. | 6-CH$_3$O-naphth-2-yl | — | OCH$_2$ | 1 | 1 | — | 107-109 | 466 (MH+) |
| 58. | 7-CH$_3$O-naphth-2-yl | — | OCH$_2$ | 1 | 1 | — | 120-122 | 466 (MH+) |
| 59. | 6-NC-naphth-2-yl | — | OCH$_2$ | 1 | 1 | — | 106-108 | 461 (MH+) |
| 60. | 4-phenyl-phenyl | — | O(CH$_2$)$_2$ | 1 | 1 | — | 97-99 | 476 (MH+) |
| 61. | 4-Cl-naphth-1-yl | — | O(CH$_2$)$_2$ | 1 | 1 | — | 86-88 | 483 (M+) |
| 62. | 6-Br-pyridin-2-yl | — | NH | 1 | 1 | HCl | 163-167 | 450 (MH+) |
| 63. | 5-NC-pyridin-2-yl | — | NH | 1 | 1 | — | 138-140 | 397 (MH+) |
| 64. | 5-H$_2$NCO-pyridin-2-yl | — | NH | 1 | 1 | — | 193-195 | 415 (MH+) |
| 65. | 5-CF$_3$-pyridin-2-yl | — | NH | 1 | 1 | HCl | 225-235 | 440 (MH+) |
| 66. | 4-CF$_3$-pyrimidin-2-yl | — | NH | 1 | 1 | — | 111-115 | 441 (MH+) |
| 67. | 2-Br-pyrimidin-4-yl | — | NH | 1 | 1 | — | 147-149 | 451 (MH+) |
| 68. | 6-(4-F-phenyl)pyridin-2-yl | — | NH | 1 | 1 | — | 91-93 | 466 (MH+) |
| 69. | 6-(3-NC-phenyl)pyridin-2-yl | — | NH | 1 | 1 | — | 113-115 | 473 (MH+) |
| 70. | 2-(3-NC-phenyl)pyrimidin-4-yl | — | NH | 1 | 1 | — | 151-153 | 474 (MH+) |
| 71. | 6-Cl-pyridin-2-yl | — | NHCH$_2$ | 1 | 1 | — | 57-59 | 420 ((M − H)−) |
| 72. | pyridin-4-yl | — | S | 1 | 1 | oil | — | 389 (MH+) |
| 73. | phenyl | — | SO$_2$ | 1 | 1 | oil | — | 437 (MNH$_4$+) |
| 74. | 4-F-phenyl | — | CO | 1 | 1 | oil | — | 402 (MH+) |
| 75. | 4-Cl-phenyl | — | CO | 1 | 1 | oil | — | 418 (MH+) |
| 76. | 4-Cl-phenyl | — | CONH | 1 | 1 | — | 156-157 | 431 ((M − H)−) |
| 77. | 4-CH$_3$-phenyl | — | CONH | 1 | 1 | — | 194-195 | 413 (MH+) |
| 78. | indol-1-yl | — | CONH | 1 | 1 | — | 158-160 | 436 ((M − H)−) |
| 79. | 3-Cl-benzo[b]thiophen-2-yl | — | CONH | 1 | 1 | — | 146-147 | 487 ((M − H)−) |
| 80. | 4-Cl-phenyl | OCH$_2$ | CONH | 1 | 1 | — | 115-116 | 461 ((M − H)−) |
| 81. | phenyl | (E)—CH=CH | CONH | 0 | 0 | — | 134-135 | 397 (MH+) |
| 82. | phenyl | (E)—CH=CH | CONH | 1 | 1 | — | 143-145 | 425 (MH+) |
| 83. | 4-Cl-phenyl | — | CONHCH$_2$ | 1 | 1 | — | 149-151 | 447 (MH+) |
| 84. | indol-1-yl | — | CONHCH$_2$ | 1 | 1 | — | 145-147 | 452 (MH+) |
| 85. | 3-Cl-benzo[b]thiophen-2-yl | — | CONHCH$_2$ | 1 | 1 | — | 126-127 | 503 (MH+) |
| 86. | 4-Cl-phenyl | OCH$_2$ | CONHCH$_2$ | 1 | 1 | — | 81-82 | 477 (MH+) |
| 87. | 4-Cl-phenyl | OC(CH$_3$)$_2$ | CONHCH$_2$ | 1 | 1 | — | 77-78 | 505 (MH+) |
| 88. | phenyl | (E)—CH=CH | CONHCH$_2$ | 0 | 1 | — | 125-126 | 425 (MH+) |
| 89. | phenyl | (E)—CH=CH | CONHCH$_2$ | 1 | 1 | — | 137-138 | 439 (MH+) |
| 90. | 4-Cl-phenyl | OCH$_2$ | CONHCH$_2$ | 0 | 1 | oil | — | 463 (MH+) |
| 91. | indol-1-yl | — | CONH(CH$_2$)$_2$ | 1 | 1 | — | 113-115 | 466 (MH+) |
| 92. | phenyl | CH$_2$ | CONH(CH$_2$)$_2$ | 0 | 0 | — | 78-79 | 413 (MH+) |
| 93. | 4-Cl-phenyl | OCH$_2$ | CONH(CH$_2$)$_2$ | 0 | 0 | oil | — | 463 (MH+) |
| 94. | phenyl | (E)—CH=CH | CONH(CH$_2$)$_2$ | 0 | 0 | — | 119-120 | 425 (MH+) |
| 95. | 2-CH$_3$O-5-Br-phenyl | — | SO$_2$NH | 0 | 0 | — | 61 | 515 (MH+) |
| 96. | 2-F-4-Br-phenyl | — | SO$_2$NH | 0 | 0 | — | 96-97 | 502 ((M − H)−) |
| 97. | indan-5-yl | — | SO$_2$NH | 0 | 0 | — | 88-89 | 445 ((M − H)−) |
| 98. | 4-phenyl-phenyl | — | SO$_2$NH | 0 | 0 | — | 146-147 | 481 ((M − H)−) |

TABLE 1-continued

| No. | R | Z | A | m | n | Salt | M.p. (°C.) | LC/MS (m/z) |
|---|---|---|---|---|---|---|---|---|
| 99. | 4-CH₃-naphth-1-yl | — | SO₂NH | 0 | 0 | — | 163-164 | 471 (MH+) |
| 100. | 5-Cl-thien-2-yl | — | SO₂NH | 0 | 0 | — | 151-152 | 445 ((M − H)−) |
| 101. | 5-Br-thien-2-yl | — | SO₂NH | 0 | 0 | — | 125-126 | 489 ((M − H)−) |
| 102. | benzo[b]thiophen-2-yl | — | SO₂NH | 0 | 0 | — | 189-190 | 427 (MH+) |
| 103. | 3-Cl-phenyl | — | SO₂NH | 1 | 1 | — | 115-116 | 467 (MH+) |
| 104. | 4-Cl-phenyl | — | SO₂NH | 1 | 1 | — | 153-155 | 469 (MH+) |
| 105. | 2-CH₃O-5-Br-phenyl | — | SO₂NH | 1 | 1 | — | 149-150 | 541 ((M − H)−) |
| 106. | naphth-1-yl | — | SO₂NH | 1 | 1 | — | 117-118 | 483 ((M − H)−) |
| 107. | naphth-2-yl | — | SO₂NH | 1 | 1 | — | 157-158 | 483 ((M − H)−) |
| 108. | phenyl | CH₂ | SO₂NH | 0 | 0 | — | 118-119 | 419 ((M − H)−) |
| 109. | phenyl | CH₂ | SO₂NH | 1 | 1 | — | 143-145 | 449 (MH+) |
| 110. | 4-Cl-phenyl | — | SO₂NHCH₂ | 0 | 0 | — | 98-99 | 455 (MH+) |
| 111. | 3-Cl-phenyl | — | SO₂NHCH₂ | 0 | 1 | — | 61-62 | 469 (MH+) |
| 112. | 4-Cl-phenyl | — | SO₂NHCH₂ | 0 | 1 | — | 117-118 | 469 (MH+) |
| 113. | naphth-1-yl | — | SO₂NHCH₂ | 0 | 1 | — | 135-136 | 485 (MH+) |
| 114. | naphth-2-yl | — | SO₂NHCH₂ | 0 | 1 | — | 134-135 | 485 (MH+) |
| 115. | phenyl | — | SO₂NHCH₂ | 1 | 1 | — | 82-84 | 449 (MH+) |
| 116. | 2-F-phenyl | — | SO₂NHCH₂ | 1 | 1 | — | 108-110 | 467 (MH+) |
| 117. | 4-F-phenyl | — | SO₂NHCH₂ | 1 | 1 | — | 103-105 | 467 (MH+) |
| 118. | 2-Cl-phenyl | — | SO₂NHCH₂ | 1 | 1 | — | 98-100 | 483 (MH+) |
| 119. | 3-Cl-phenyl | — | SO₂NHCH₂ | 1 | 1 | — | 59-60 | 481 ((M − H)−) |
| 120. | 4-Cl-phenyl | — | SO₂NHCH₂ | 1 | 1 | — | 136-138 | 483 (MH+) |
| 121. | 2-CH₃-phenyl | — | SO₂NHCH₂ | 1 | 1 | — | 81-83 | 463 (MH+) |
| 122. | 3-CH₃-phenyl | — | SO₂NHCH₂ | 1 | 1 | — | 96-98 | 463 (MH+) |
| 123. | 4-CH₃-phenyl | — | SO₂NHCH₂ | 1 | 1 | — | 115-117 | 463 (MH+) |
| 124. | 2-CF₃-phenyl | — | SO₂NHCH₂ | 1 | 1 | — | 83-85 | 517 (MH+) |
| 125. | 3-CF₃-phenyl | — | SO₂NHCH₂ | 1 | 1 | — | 103-105 | 515 ((M − H)−) |
| 126. | 4-CF₃-phenyl | — | SO₂NHCH₂ | 1 | 1 | — | 115-117 | 517 (MH+) |
| 127. | 2-CH₃O-phenyl | — | SO₂NHCH₂ | 1 | 1 | — | 86-88 | 479 (MH+) |
| 128. | 3-CH₃O-phenyl | — | SO₂NHCH₂ | 1 | 1 | — | 98-100 | 477 ((M − H)−) |
| 129. | 4-CH₃O-phenyl | — | SO₂NHCH₂ | 1 | 1 | — | 131-133 | 479 (MH+) |
| 130. | 3-CF₃O-phenyl | — | SO₂NHCH₂ | 1 | 1 | oil | — | 533 (MH+) |
| 131. | 4-CF₃O-phenyl | — | SO₂NHCH₂ | 1 | 1 | — | 109-110 | 533 (MH+) |
| 132. | 3-NC-phenyl | — | SO₂NHCH₂ | 1 | 1 | — | 118-120 | 474 (MH+) |
| 133. | 4-NC-phenyl | — | SO₂NHCH₂ | 1 | 1 | — | 148-150 | 472 ((M − H)−) |
| 134. | 2-F-3-Cl-phenyl | — | SO₂NHCH₂ | 1 | 1 | — | 98-100 | 501 (MH+) |
| 135. | 2-Cl-3-Cl-phenyl | — | SO₂NHCH₂ | 1 | 1 | — | 88-90 | 517 (MH+) |
| 136. | 2-CF₃-4-F-phenyl | — | SO₂NHCH₂ | 1 | 1 | — | 110-111 | 533 ((M − H)−) |
| 137. | 3-F-4-CH₃-phenyl | — | SO₂NHCH₂ | 1 | 1 | — | 118-119 | 483 (MH+) |
| 138. | 3-F-4-CH₃-phenyl | — | SO₂NHCH₂ | 1 | 1 | — | 94-96 | 479 ((M − H)−) |
| 139. | 3-Cl-4-F-phenyl | — | SO₂NHCH₂ | 1 | 1 | — | 144-146 | 499 (MH+) |
| 140. | 3-Cl-4-Cl-phenyl | — | SO₂NHCH₂ | 1 | 1 | — | 105-106 | 515 ((M − H)−) |
| 141. | 3-Cl-4-CH₃-phenyl | — | SO₂NHCH₂ | 1 | 1 | — | 99-100 | 495 ((M − H)−) |
| 142. | 3-Cl-4-CF₃O-phenyl | — | SO₂NHCH₂ | 1 | 1 | — | 101-103 | 565 ((M − H)−) |
| 143. | 3-CH₃-4-CH₃-phenyl | — | SO₂NHCH₂ | 1 | 1 | — | 134-136 | 475 (MH+) |
| 144. | 3-F-4-CH₃O-phenyl | — | SO₂NHCH₂ | 1 | 1 | — | 115-116 | 497 (MH+) |
| 145. | 3-CH₃-4-F-phenyl | — | SO₂NHCH₂ | 1 | 1 | — | 117-119 | 479 ((M − H)−) |
| 146. | 3-CH₃O-4-F-phenyl | — | SO₂NHCH₂ | 1 | 1 | — | 131-132 | 497 (MH+) |
| 147. | 3-CF₃-4-F-phenyl | — | SO₂NHCH₂ | 1 | 1 | — | 112-113 | 533 ((M − H)−) |
| 148. | 3-CF₃-4-Cl-phenyl | — | SO₂NHCH₂ | 1 | 1 | — | 108-109 | 549 ((M − H)−) |
| 149. | 4-CH₃SO₂-phenyl | — | SO₂NHCH₂ | 1 | 1 | — | 180-181 | 527 (MH+) |
| 150. | 4-(pyrrolidin-1-yl)-SO₂-phenyl | — | SO₂NHCH₂ | 1 | 1 | — | 198-199 | 582 (MH+) |
| 151. | 4-phenylphenyl | — | SO₂NHCH₂ | 1 | 1 | — | 137-138 | 525 (MH+) |
| 152. | naphth-1-yl | — | SO₂NHCH₂ | 1 | 1 | — | 155-156 | 499 (MH+) |
| 153. | naphth-2-yl | — | SO₂NHCH₂ | 1 | 1 | — | 113-114 | 499 (MH+) |
| 154. | benzo[b]thiophen-3-yl | — | SO₂NHCH₂ | 1 | 1 | — | 128-130 | 505 (MH+) |
| 155. | 3-CH₃-5-CH₃-isoxazol-4-yl | — | SO₂NHCH₂ | 1 | 1 | oil | 101-103 | 466 ((M − H)−) |
| 156. | 4-(oxazol-5-yl)phenyl | — | SO₂NHCH₂ | 1 | 1 | — | 121-122 | 514 ((M − H)−) |
| 157. | 4-Cl-phenyl | CH₂ | SO₂NHCH₂ | 1 | 1 | — | 100-102 | 495 ((M − H)−) |
| 158. | 4-Cl-phenyl | — | SO₂NHC-(c-prop) | | | — | 150-152 | 509 (MH+) |
| 159. | 4-CH₃O-phenyl | — | SO₂NHC-(c-prop) | | | — | 142-144 | 505 (MH+) |
| 160. | 3-Cl-phenyl | — | SO₂NH(CH₂)₂ | 0 | 0 | — | 71-72 | 469 (MH+) |
| 161. | 4-Cl-phenyl | — | SO₂NH(CH₂)₂ | 0 | 0 | — | 112-113 | 469 (MH+) |
| 162. | naphth-1-yl | — | SO₂NH(CH₂)₂ | 0 | 0 | — | 124-125 | 485 (MH+) |
| 163. | naphth-2-yl | — | SO₂NH(CH₂)₂ | 0 | 0 | — | 130-131 | 485 (MH+) |
| 164. | phenyl | — | OCONH | 1 | 1 | — | 146-148 | 413 ((M − H)−) |
| 165. | phenyl | — | NHCONH | 1 | 1 | — | 203-205 | 414 (MH+) |
| 166. | 3-Cl-phenyl | — | NHCONH | 1 | 1 | — | 204-206 | 448 (MH+) |
| 167. | 4-Cl-phenyl | — | NHCONH | 1 | 1 | — | 182-184 | 448 (MH+) |
| 168. | 3-NC-phenyl | — | NHCONH | 1 | 1 | — | 173-175 | 439 (MH+) |
| 169. | 4-NC-phenyl | — | NHCONH | 1 | 1 | — | 108-112 | 439 (MH+) |
| 170. | 2-F-4-phenyl | — | NHCONH | 1 | 1 | — | 158-160 | 450 (MH+) |
| 171. | 2-Cl-4-Cl-phenyl | — | NHCONH | 1 | 1 | — | 183-185 | 482 (MH+) |
| 172. | 2-Cl-5-Cl-phenyl | — | NHCONH | 1 | 1 | — | 179-181 | 482 (MH+) |
| 173. | 2-CH₃O-5-Cl-phenyl | — | NHCONH | 1 | 1 | — | 172-174 | 478 (MH+) |
| 174. | 3-CH₃SO₂-phenyl | — | NHCONH | 1 | 1 | — | 170-174 | 492 (MH+) |
| 175. | 3-H₂NCO-phenyl | — | NHCONH | 1 | 1 | — | 202-204 | 457 (MH+) |

TABLE 1-continued

| No. | R | Z | A | m | n | Salt | M.p. (° C.) | LC/MS (m/z) |
|---|---|---|---|---|---|---|---|---|
| 176. | phenyl | CH$_2$ | NHCONH | 1 | 1 | — | 163-165 | 428 (MH+) |
| 177. | 4-Cl-phenyl | — | NHCONHCH$_2$ | 0 | 0 | — | 150-151 | 434 (MH+) |
| 178. | 3-Cl-phenyl | — | NHCONHCH$_2$ | 0 | 1 | — | 130-131 | 448 (MH+) |
| 179. | 4-Cl-phenyl | — | NHCONHCH$_2$ | 0 | 1 | — | 183-184 | 448 (MH+) |
| 180. | 4-NC-phenyl | — | NHCONHCH$_2$ | 0 | 1 | oil | — | 439 (MH+) |
| 181. | 4-Cl-phenyl | — | NHCONHCH$_2$ | 1 | 1 | — | 155-157 | 462 (MH+) |
| 182. | benzimidazol-5-yl | — | NHCONHCH$_2$ | 1 | 1 | — | 143-145 | 468 (MH+) |
| 183. | indazol-6-yl | — | NHCONHCH$_2$ | 1 | 1 | — | 83-85 | 468 (MH+) |
| 184. | 2-(4-CF$_3$-phenyl)thiazol-4-yl | — | NHCONHCH$_2$ | 1 | 1 | — | 183-184 | 579 (MH+) |
| 185. | phenyl | CH$_2$ | NHCONHCH$_2$ | 0 | 1 | — | 86-87 | 428 (MH+) |
| 186. | phenyl | CH$_2$ | NHCONHCH$_2$ | 1 | 1 | — | 162-164 | 442 (MH+) |
| 187. | phenyl | — | N(CH$_3$)CONHCH$_2$ | 0 | 1 | — | 101-102 | 428 (MH+) |
| 188. | 3-Cl-phenyl | — | NHCONH(CH$_2$)$_2$ | 0 | 0 | — | 116-117 | 448 (MH+) |
| 189. | 4-Cl-phenyl | — | NHCONH(CH$_2$)$_2$ | 0 | 0 | — | 119-120 | 448 (MH+) |
| 190. | 4-NC-phenyl | — | NHCONH(CH$_2$)$_2$ | 0 | 0 | oil | — | 439 (MH+) |
| 191. | phenyl | — | N(CH$_3$)CONH(CH$_2$)$_2$ | 0 | 0 | — | 101-102 | 428 (MH+) |
| 192. | 4-Cl-phenyl | — | NHCONH(CH$_2$)$_2$ | 1 | 1 | — | 159-161 | 476 (MH+) |
| 193. | phenyl | CH$_2$ | NHCONH(CH$_2$)$_2$ | 0 | 0 | — | 105-106 | 428 (MH+) |
| 194. | 4-Cl-phenyl | — | SO$_2$NHCO | 1 | 1 | — | 166-167 | 495 ((M − H)−) |
| 195. | 4-Cl-phenyl | — | SO$_2$NHCONH | 1 | 1 | — | 173-174 | 510 ((M − H)−) |
| 196. | 4-Cl-phenyl | — | SO$_2$NHCONHCH$_2$ | 1 | 1 | — | 156-157 | 524 ((M − H)−) |
| 197. | 4-H$_2$NCO-phenyl | — | OCH$_2$ | 1 | 1 | — | 169-171 | 429 (MH+) |
| 198. | 3-H$_2$NCO-phenyl | — | O(CH$_2$)$_2$ | 1 | 1 | — | 102-106 | 443 (MH+) |
| 199. | 4-H$_2$NCO-phenyl | — | O(CH$_2$)$_2$ | 1 | 1 | — | 125-127 | 443 (MH+) |
| 200. | 4-CH$_3$SO$_2$-phenyl | — | SO$_2$NH | 1 | 1 | — | 173-175 | 511 ((M − H)−) |
| 201. | pyridin-3-yl | — | SO$_2$NH | 1 | 1 | — | 162-164 | 436 (MH+) |
| 202. | 2-CF$_3$O-phenyl | — | SO$_2$NHCH$_2$ | 1 | 1 | — | 72-74 | 533 (MH+) |
| 203. | 2-CH$_3$O-4-CH$_3$-phenyl | — | SO$_2$NHCH$_2$ | 1 | 1 | — | 122-124 | 493 (MH+) |
| 204. | 2,4-(OCH$_3$)$_2$-phenyl | — | SO$_2$NHCH$_2$ | 1 | 1 | — | 123-125 | 509 (MH+) |
| 205. | 2-CH$_3$O-5-CH$_3$O-phenyl | — | SO$_2$NHCH$_2$ | 1 | 1 | — | 81-83 | 509 (MH+) |
| 206. | 2-CH$_3$O-5-F-phenyl | — | SO$_2$NHCH$_2$ | 1 | 1 | — | 138-140 | 497 (MH+) |
| 207. | 2-CH$_3$O-5-CH$_3$SO$_2$-phenyl | — | SO$_2$NHCH$_2$ | 1 | 1 | — | 82-84 | 557 (MH+) |
| 208. | 2,5-(CH$_3$)2-4-Cl-phenyl | — | SO$_2$NHCH$_2$ | 1 | 1 | — | 122-124 | 509 ((M − H)−) |
| 209. | 3-(5-CH$_3$-1,3,4-oxadiazol-2-yl)-phenyl | — | SO$_2$NHCH$_2$ | 1 | 1 | — | 138-140 | 531 (MH+) |
| 210. | 2,3-dihydrobenzo[1,4]dioxan-6-yl | — | SO$_2$NHCH$_2$ | 1 | 1 | — | 122-124 | 507 (MH+) |
| 211. | benzo[1,2,5]thiadiazol-4-yl | — | SO$_2$NHCH$_2$ | 1 | 1 | — | 146-148 | 507 (MH+) |
| 212. | 4-CH$_3$-3,4-dihydro-2H-benz[1,4]oxazin-7-yl | — | SO$_2$NHCH$_2$ | 1 | 1 | — | 118-120 | 520 (MH+) |
| 213. | 3-(2-CH$_3$-pyrimidin-4-yl)phenyl | — | SO$_2$NHCH$_2$ | 1 | 1 | — | 135-137 | 541 (MH+) |
| 214. | 1,3-(CH$_3$)$_2$-5-Cl-pyrazol-4-yl | — | SO$_2$NHCH$_2$ | 1 | 1 | — | 86-88 | 501 (MH+) |
| 215. | pyridin-3-yl | — | SO$_2$NHCH$_2$ | 1 | 1 | — | 92-94 | 450 (MH+) |
| 216. | 6-Cl-pyridin-3-yl | — | SO$_2$NHCH$_2$ | 1 | 1 | — | 144-146 | 482 ((M − H)−) |
| 217. | 4-Cl-phenyl | — | SO$_2$N(CH$_3$)CH$_2$ | 1 | 1 | oil | — | 497 (MH+) |
| 218. | 4-CH$_3$SO$_2$-phenyl | — | SO$_2$NH(CH$_2$)$_2$ | 1 | 1 | — | 113-115 | 541 (MH+) |
| 219. | pyridin-3-yl | — | SO$_2$NH(CH$_2$)$_2$ | 1 | 1 | — | 103-105 | 464 (MH+) |
| 220. | 4-Cl-phenyl | — | SO$_2$NHC-(c-prop) | 0 | 0 | — | 108-109 | 481 (MH+) |
| 221. | 2-CH$_3$O-5-CH$_3$SO$_2$-phenyl | — | SO$_2$NHC-(c-prop) | 0 | 0 | — | 98-100 | 572 (MNH$_4$+) |
| 222. | pyridin-3-yl | — | SO$_2$NHC-(c-prop) | 0 | 0 | — | 122-124 | 448 (MH+) |
| 223. | 4-CH$_3$SO$_2$-phenyl | — | SO$_2$NHC-(c-prop) | 0 | 0 | — | 198-200 | 525 (MH+) |
| 224. | 4-CH$_3$SO$_2$-phenyl | — | NHCH$_2$ | 1 | 1 | — | 107-109 | 504 (MH + ACN) |
| 225. | 4-H$_2$NSO$_2$-phenyl | — | NHCH$_2$ | 1 | 1 | — | 184-186 | 464 (MH+) |
| 226. | 2-H$_2$NCO-pyridin-4-yl | — | NHCH$_2$ | 1 | 1 | — | 160-163 | 429 (MH+) |
| 227. | 4-H$_2$NCO-pyridin-2-yl | — | NHCH$_2$ | 1 | 1 | — | 143-145 | 429 (MH+) |
| 228. | 5-H$_2$NCO-pyridin-2-yl | — | NHCH$_2$ | 1 | 1 | — | 146-148 | 429 (MH+) |
| 229. | 6-H$_2$NCO-pyridin-2-yl | — | NHCH$_2$ | 1 | 1 | — | 50-60 | 429 (MH+) |
| 230. | 5-H$_2$NCO-pyrazin-2-yl | — | NHCH$_2$ | 1 | 1 | — | 187-189 | 430 ((M − H)−) |
| 231. | 4-H$_2$NCO-pyrazol-1-yl | CH$_2$ | — | 1 | 1 | — | 98-118 | 403 (MH+) |
| 232. | 5-H$_2$NCO-pyridin-2-yl | — | NH(CH$_2$)$_2$ | 1 | 1 | — | 148-150 | 443 (MH+) |
| 233. | 4-H$_2$NCO-pyrimidin-2-yl | — | NH(CH$_2$)$_2$ | 1 | 1 | — | 145-147 | 444 (MH+) |
| 234. | 5-H$_2$NCO-pyrazin-2-yl | — | NH(CH$_2$)$_2$ | 1 | 1 | — | 156-158 | 444 (MH+) |
| 235. | 6-H$_2$NCO-pyrazin-2-yl | — | NH(CH$_2$)$_2$ | 1 | 1 | — | 156-158 | 444 (MH+) |
| 236. | 2,3-dihydrobenz[1,4]oxazin-4-yl | — | CONH | 1 | 1 | — | 123-125 | 456 (MH+) |
| 237. | 2,3-dihydrobenz[1,4]oxazin-4-yl | — | CONHCH$_2$ | 1 | 1 | — | 35-37 | 470 (MH+) |
| 238. | 3-CH$_3$SO$_2$-phenyl | — | CONH(CH$_2$)$_2$ | 1 | 1 | — | 115-117 | 505 (MH+) |
| 239. | 4-CH$_3$SO$_2$-phenyl | — | CONH(CH$_2$)$_2$ | 1 | 1 | — | 112-114 | 505 (MH+) |
| 240. | 4-H$_2$NSO$_2$-phenyl | — | CONH(CH$_2$)$_2$ | 1 | 1 | — | 176-178 | 506 (MH+) |
| 241. | 2,3-dihydrobenz[1,4]oxazin-4-yl | — | CONH(CH$_2$)$_2$ | 1 | 1 | oil | — | 484 (MH+) |
| 242. | benzimidazol-5-yl | — | NHCONH | 1 | 1 | — | 172-174 | 454 (MH+) |
| 243. | 1-CH$_3$SO$_2$-indolin-5-yl | — | NHCONH | 1 | 1 | — | 103-105 | 533 (MH+) |
| 244. | indazol-6-yl | — | NHCONH | 1 | 1 | — | 118-120 | 454 (MH+) |
| 245. | 2-CH$_3$O-5-CH$_3$SO$_2$-phenyl | — | NHCONHCH$_2$ | 1 | 1 | — | 106-108 | 536 (MH+) |
| 246. | 2-CH$_3$O-5-(pyrrolidin-1-yl-SO$_2$)-phenyl | — | NHCONHCH$_2$ | 1 | 1 | — | 96-98 | 591 (MH+) |
| 247. | 1-CH$_3$SO$_2$-indolin-5-yl | — | NHCONHCH$_2$ | 1 | 1 | — | 88-90 | 547 (MH+) |

TABLE 2

| No. | Rt (min) | Method |
|---|---|---|
| 2 | 2.37 | E |
| 3 | 2.39 | E |
| 4 | 2.29 | E |
| 6 | 1.77 | E |
| 7 | 2.42 | E |
| 16 | 2.37 | E |
| 18 | 11.8 | B |
| 19 | 11.4 | B |
| 21 | 1.47 | D |
| 26 | 10.2 | B |
| 29 | 12.4 | B |
| 37 | 12.2 | B |
| 38 | 12.3 | B |
| 44 | 1.26 | E |
| 72 | 1.32 | E |
| 73 | 1.88 | E |
| 74 | 2.10 | E |
| 75 | 10.0 | B |
| 90 | 1.28 | D |
| 93 | 1.29 | D |
| 130 | 1.40 | D |
| 217 | 5.38 | C |
| 241 | 1.35 | D |

TABLE 3

| No. | Enantiomer | $[\alpha]_D$ | Conditions |
|---|---|---|---|
| 22 | (S) | +20° | DMSO, conc. 0.159 g/100 ml, 20° C. |
| 23 | (R) | −15° | DMSO, conc. 0.145 g/100 ml, 20° C. |
| 24 | (S) | +29° | MeOH, conc. 0.310 g/100 ml, 20° C. |
| 25 | (R) | −30° | MeOH, conc. 0.484 g/100 ml, 20° C. |

The compounds according to the invention surprisingly exhibit an inhibitory effect with regard to the enzyme MGL (monoacyl glycerol lipase). The enzyme MGL catalyses the hydrolysis of endogenous derivatives of monoglyceride esters of various fatty acids (FEBS Letters, 1998, 429, 152-156) and in particular the hydrolysis of 2-arachidonoylglycerol (2-AG) and of 1(3)-arachidonoylglycerol (1(3)-AG) (J. Biol. Chem., 1987, 272 (48), 27218-27223; Proc. Natl. Acad. Sci. USA, 2002, 99 (16), 10819-10824; Biochem. Pharmacol., 2004, 67, 1381-1387; Mol. Pharmacol., 2004, 66 (5), 1260-1264). The 2-AG and 1(3)-AG derivatives in particular interact with cannabinoid receptors (J. Biol. Chem., 1999, 274 (5), 2794-2801; J. Biol. Chem., 2000, 275 (1), 605-612; British J. Pharmacol., 2001, 134, 664-672).

The compounds of the invention block this decomposition pathway and increase the tissue levels of these derivatives, in particular of 2-AG and/or 1(3)-AG. They can therefore be used in the prevention and treatment of pathologies in which 2-AG and/or 1(3)-AG, in particular, and/or any other substrate metabolized with the enzyme MGL are implicated (Progress in Lipid Research, 2006, 45, 405-446; Nature Reviews Drug Discovery, 2008, 7, 438-455).

The compounds according to the invention have formed the subject of pharmacological tests which make it possible to determine their inhibitory effect on the enzyme MGL.

Tests have consisted in measuring the in vitro activity of the compounds of the invention with regard to the enzyme MGL.

The inhibitory activity with respect to MGL is given by the concentration which inhibits 50% of the activity of MGL.

The inhibitory activity was measured in a radioenzymatic assay based on measuring the product of hydrolysis of 2-oleoylglycerol ([$^3$H]2-OG) by the enzyme MGL. The products of hydrolysis of [$^3$H]2-OG, labelled on the glycerol, are oleic acid and [$^3$H]glycerol. The source of enzyme MGL is a homogenate of mouse brain from which the cerebellum and the medulla oblongata have been removed. The mouse brains are removed and stored at −80° C. until they are used or homogenized immediately for 2 times 5 seconds using a Precellys device (Bertin) at 5000 rpm in a 10 mM Tris-HCl pH 8, 150 mM NaCl, 1 mM EDTA buffer at 4° C. The concentration of the homogenates is subsequently adjusted to 3.75 µg/µl.

The dilution series of the compounds is prepared from stock solutions at 20 mM in 100% DMSO. The first dilution of this series is prepared in 100% DMSO and then the second is prepared in the enzymatic reaction buffer (50 mM phosphate, 0.1% BSA), resulting in the preparation of a 10-times concentrated concentration range. The test compounds are preincubated at the chosen concentration for 20 minutes with the mouse brain homogenate preparation. The final concentration of DMSO in the enzymatic reaction does not exceed 0.1%.

Assaying of the MGL activity is carried out at ambient temperature in a 96-well microplate in a final reaction volume of 50 µl. Briefly, 37.5 µg of proteins are diluted in 50 mM of phosphate buffer comprising 0.1% of BSA. After 20 minutes of preincubation with the test compounds, the proteins are incubated for 20 minutes in the presence of 50 µM of 2-OG comprising an amount of [$^3$H]2-OG of 0.027 µCi per well (specific activity of 20 Ci/mmol). The reaction is stopped by the addition of 50 µl per well of a charcoal suspension (6% of Sigma activated charcoal, reference C4386, in suspension in a 0.5M HCl, 1.5M NaCl solution). After stirring for 10 minutes, the [$^3$H]glycerol, not retained by the charcoal, is collected by filtration in a microplate comprising 100 µl of scintillant (OptiPhase Supermix, Perkin-Elmer) per well. The radioactivity present in each well is counted for 5 minutes by liquid scintillation (Wallac 1450 MicroBeta).

Under these conditions, the most active compounds of the invention exhibit an $IC_{50}$ (concentration which inhibits the control enzymatic activity of the MGL by 50%) of between 0.0001 and 0.1 µM.

For example, compounds Nos. 13, 33, 70, 120, 161, 188 and 211 showed an $IC_{50}$ of 0.006, 0.0006, 0.005, 0.004, 0.0014, 0.0011 and 0.007 µM respectively.

It is thus apparent that the compounds according to the invention have an inhibitory activity with respect to MGL.

The compounds according to the invention can thus be used in the preparation of medicaments, in particular of medicaments which are inhibitors of the enzyme MGL.

Thus, according to another of its aspects, a subject-matter of the invention is medicaments which comprise a compound of formula (I) or an addition salt of the latter with a pharmaceutically acceptable acid or also a hydrate or a solvate of the compound of formula (I).

These medicaments are employed therapeutically, in particular in the treatment and the prevention of:

pain, in particular acute or chronic pain of neurogenic type: migraine, neuropathic pain, including forms associated with the herpes virus and with diabetes;

acute or chronic pain associated with inflammatory diseases: arthritis, rheumatoid arthritis, osteoarthritis, spondylitis, gout, vasculitis, Crohn's disease, irritable bowel syndrome;

acute or chronic peripheral pain;

dizziness, vomiting, nausea, in particular that resulting from chemotherapy;

eating disorders, in particular anorexia and cachexia of various natures;

metabolic syndrome and its manifestations, including obesity;

dyslipidaemia and its manifestations, including atherosclerosis and coronary diseases;

neurological and psychiatric pathologies: tremors, dyskinesias, dystonias, spasticity, obsessive-compulsive behaviour, Tourette's syndrome, all forms of depression and of anxiety of any nature and origin, mood disorders, psychoses;

acute or chronic neurodegenerative diseases: Parkinson's disease, Alzheimer's disease, senile dementia, Huntington's chorea, lesions related to cerebral ischaemia and to cranial and medullary trauma, amyotrophic lateral sclerosis;

epilepsy;

sleep disorders, including sleep apnoea;

cardiovascular diseases, in particular hypertension, cardiac arrhythmias, arteriosclerosis, heart attack, cardiac ischaemia;

renal ischaemia;

cancers: benign skin tumours, brain tumours and papillomas, prostate tumours, cerebral tumours (glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, epiphyseal tumour, ependymoblastomas, malignant meningiomas, sarcomatosis, malignant melanomas, schwannomas);

disorders of the immune system, in particular autoimmune diseases: psoriasis, lupus erythematosus, diseases of the connective tissue or collagen diseases, Sjögren's syndrome, ankylosing spondylitis, undifferentiated spondylitis, Behcet's disease, autoimmune haemolytic anaemia, multiple sclerosis, amyotrophic lateral sclerosis, amyloidosis, graft rejection, diseases affecting the plasmocytic line;

allergic diseases: immediate or delayed hypersensitivity, allergic rhinitis or conjunctivitis, contact dermatitis;

parasitic, viral or bacterial infectious diseases: AIDS, meningitis;

inflammatory diseases, in particular joint diseases: arthritis, rheumatoid arthritis, osteoarthritis, spondylitis, gout, vasculitis, Crohn's disease, irritable bowel syndrome;

osteoporosis;

eye conditions: ocular hypertension, glaucoma, degeneration and apoptosis of retinal ganglion cells and neuroretinal cells;

pulmonary conditions: diseases of the respiratory tract, bronchospasm, coughing, asthma, chronic bronchitis, chronic obstruction of the respiratory tract, emphysema;

gastrointestinal diseases: irritable bowel syndrome, inflammatory intestinal disorders, ulcers, diarrhoea;

urinary incontinence and bladder inflammation.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt or a hydrate or a solvate of the said compound, and also at least one pharmaceutically acceptable excipient.

The said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its optional salt, solvate or hydrate can be administered in a unit administration form, as a mixture with conventional pharmaceutical excipients, to animals and to man for the prophylaxis or the treatment of the above disorders or diseases.

Appropriate unit administration forms comprise oral forms, such as tablets, soft or hard gelatin capsules, powders, granules and oral solutions or suspensions, forms for sublingual, buccal, intratracheal, intraocular or intranasal administration or for administration by inhalation, forms for topical, transdermal, subcutaneous, intramuscular or intravenous administration, forms for rectal administration and implants. For topical application, the compounds according to the invention can be used in creams, gels, ointments or lotions.

By way of example, a unit administration form of a compound according to the invention in the form of a tablet can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

According to another of its aspects, the present invention also relates to a method for the treatment of the pathologies indicated above which comprises the administration, to a patient, of an effective dose of a compound according to the invention or one of its pharmaceutically acceptable salts or its hydrates or its solvates.

What is claimed is:

1. A compound of formula (I):

wherein:

R represents an $R^1$ group unsubstituted or substituted by one or more substituents independently selected from the group consisting of $R^2$ and $R^3$;

$R^1$ represents an aryl or heteroaryl group;

$R^2$ represents a halogen atom or a cyano, nitro, oxo, ($C_1$-$C_6$)alkyl, ($C_1$-$C_6$)alkoxy, hydroxyl, ($C_1$-$C_6$)alkylthio, ($C_1$-$C_6$)haloalkyl, ($C_1$-$C_6$)haloalkoxy, ($C_1$-$C_6$)haloalkylthio, $NR^4R^5$, $NR^4COR^5$, $NR^4SO_2R^5$, $COR^4$, $CO_2R^4$, $CONR^4R^5$, $SO_2R^4$, $SO_2NR^4R^5$, or benzyloxy group;

$R^3$ represents a monocyclic aryl or heteroaryl group which can be substituted by one or more $R^2$ groups which are identical to or different from one another;

$R^4$ and $R^5$ represent, independently of one another, a hydrogen atom or a ($C_1$-$C_6$)alkyl group or forms, with the nitrogen atom or the N—CO or N—SO$_2$ fragment which carriers them, a heterocycle optionally substituted by a ($C_1$-$C_6$)alkyl or benzyl group;

Z represents a bond, a ($C_1$-$C_6$)alkylene group, a ($C_2$-$C_6$) alkenylene group, a ($C_2$-$C_6$)alkynylene group, an O—($C_1$-$C_6$)alkylene group or an N($R^4$)—($C_1$-$C_6$)alkylene group;

A represents a bond, an oxygen atom, a sulphur atom, an N($R^4$) group, an N($R^4$)—($C_1$-$C_6$)alkylene group, a CON($R^4$) group, a CON($R^4$)—($C_1$-$C_6$)alkylene group, an SO₂N(R^A) group, an SO₂N(R^A)—(C₁-C₆)alkylene group, an OCON(R^A) group, an OCON(R^A)—(C₁-C₆) alkylene group, an N(R^B)CON(R^A) group, an N(R^B) CON(R^A)—(C₁-C₆)alkylene group, an N(R^B)SO₂N (R^A) group, an N(R^B)SO₂N(R^A)—(C₁-C₆)alkylene group, an O—(C₁-C₆)alkylene group, an N(R^B)CO₂ group, an N(R^B)CO₂—(C₁-C₆)alkylene group, an S—(C₁-C₆)alkylene group, an SO₂ group, an SO₂(C₁-C₆)alkylene group, an N(R^B)SO₂ group, an N(R^B) SO₂—(C₁-C₆)alkylene group, a CO group, a CO—(C₁-C₆)alkylene group, an N(R^B)CO group, an N(R^B)CO—(C₁-C₆)alkylene group, an SO₂N(R^B)CO group, an SO₂N(R^B)CO—(C₁-C₆)alkylene group, an SO₂N(R^B) CON(R^A) group or an SO₂N(R^B)CON(R^A)—(C₁-C₆) alkylene group;

R^A and R^B represent, independently of one another, a hydrogen atom or a (C₁-C₆)alkyl group; and m and n represent, independently of one another, an integer equal to 0 or 1, in the form of the base or of an addition salt with an acid.

2. A pharmaceutical composition comprising a compound of formula (I) according to claim 1 or a pharmaceutically acceptable salt thereof and at least one pharmaceutically acceptable excipient.

3. The compound of formula (I) according to claim 1, wherein:
R¹ represents a phenyl, naphthyl, indanyl, benzoxazole, benzisoxazole, benzimidazole, benzotriazole, oxadiazole, indazole, isoxazole, pyridine, pyrazine, pyrimidine, thienyl, thiazole, benzothiophene, indole, dihydrobenzodioxane, benzothiadiazole, pyrazole, dihydrobenzoxazine or indoline group;
R² represents one or more groups chosen from a halogen atom or a methyl, trifluoromethyl, methoxy, trifluoromethoxy, cyano, oxo, CH₃NHCO, CH₃SO₂, NH₂CO, NH₂SO₂ and pyrrolidine-SO₂ group;
R³ represents a group chosen from a phenyl and an oxazole;
or the compound 2,2,2-trifluoro-1-(trifluoromethyl)ethyl 4-{[3-(2-methylpyrimidin-4-yl)benzenesulphonylamino]methyl}piperidine-1-carboxylate; in the form of the base or of an addition salt with an acid.

4. A pharmaceutical composition comprising a compound of formula (I) or the compound 2,2,2-trifluoro-1-(trifluoromethyl)ethyl 4-{[3-(2-methylpyrimidin-4-yl)benzenesulphonylamino]methyl}piperidine-1-carboxylate according to claim 3 or a pharmaceutically acceptable salt thereof and at least one pharmaceutically acceptable excipient.

5. The compound of formula (I) according to claim 1, wherein:
Z represents a bond or a CH₂, (CH₂)₂, CH=CH, C≡C, OCH₂ or OC(CH₃)₂ group, in the form of the base or of an addition salt with an acid.

6. A pharmaceutical composition comprising a compound of formula (I) according to claim 5 or a pharmaceutically acceptable salt thereof and at least one pharmaceutically acceptable excipient.

7. The compound of formula (I) according to claim 1, wherein:
A represents a bond, an oxygen atom, a sulphur atom, an OCH₂ group, an O(CH₂)₂ group, an NH, NHCH₂ or NH(CH₂)₂ group, an SO₂ or CO group, a CONH group, a CONHCH₂ or CONH(CH₂)₂ group, an SO₂NH group, an SO₂NHCH₂ or SO₂NH(CH₂)₂ group, an SO₂NHCO, SO₂NHCONH or SO₂NHCONHCH₂ group, an OCONH group, an NHCONH group, an NHCONHCH₂ group, an N(CH₃)CONHCH₂, NHCONH(CH₂)₂ or N(CH₃)CONH(CH₂)₂ group or an SO₂N(CH₃)CH₂ group,
in the form of the base or of an addition salt with an acid.

8. A pharmaceutical composition comprising a compound of formula (I) according to claim 7 or a pharmaceutically acceptable salt thereof and at least one pharmaceutically acceptable excipient.

9. The compound of formula (I) according claim 1, wherein m and n represent 1, in the form of the base or of an addition salt with an acid.

10. A pharmaceutical composition comprising a compound of formula (I) according to claim 9 or a pharmaceutically acceptable salt thereof and at least one pharmaceutically acceptable excipient.

11. The compound of formula (I) according to claim 1, wherein m represents 1 and n represents 0, in the form of the base or of an addition salt with an acid.

12. A pharmaceutical composition comprising a compound of formula (I) according to claim 11 or a pharmaceutically acceptable salt thereof and at least one pharmaceutically acceptable excipient.

13. The compound of formula (I) according to claim 1, wherein m and n represent 0, in the form of the base or of an addition salt with an acid.

14. A pharmaceutical composition comprising a compound of formula (I) according to claim 13 or a pharmaceutically acceptable salt thereof and at least one pharmaceutically acceptable excipient.

15. The compound of formula (I) according to claim 1, wherein:
R¹ represents a phenyl, naphthyl, indanyl, benzoxazole, benzisoxazole, benzimidazole, benzotriazole, oxadiazole, indazole, isoxazole, pyridine, pyrazine, pyrimidine, thienyl, thiazole, benzothiophene, indole, dihydrobenzodioxane, benzothiadiazole, pyrazole, dihydrobenzoxazine or indoline group;
R² represents one or more groups chosen from a halogen atom or a methyl, trifluoromethyl, methoxy, trifluoromethoxy, cyano, oxo, CH₃NHCO, CH₃SO₂, NH₂CO, NH₂SO₂ and pyrrolidine-SO₂ group;
R³ represents a group chosen from a phenyl and an oxazole;
Z represents a bond or a CH₂, (CH₂)₂, CH=CH, C≡C, OCH₂ or OC(CH₃)₂ group;
A represents a bond, an oxygen atom, a sulphur atom, an OCH₂ group, an O(CH₂)₂ group, an NH, NHCH₂ or NH(CH₂)₂ group, an SO₂ or CO group, a CONH group, a CONHCH₂ or CONH(CH₂)₂ group, an SO₂NH group, an SO₂NHCH₂ or SO₂NH(CH₂)₂ group, an SO₂NHCO, SO₂NHCONH or SO₂NHCONHCH₂ group, an OCONH group, an NHCONH group, an NHCONHCH₂ group, an N(CH₃)CONHCH₂, NHCONH(CH₂)₂ or N(CH₃)CONH(CH₂)₂ group or an SO₂N(CH₃)CH₂ group; and
m and n represent, independently of one another, an integer equal to 0 or 1, in the form of the base or of an addition salt with an acid.

16. A pharmaceutical composition comprising a compound of formula (I) according to claim 15 or a pharmaceutically acceptable salt thereof and at least one pharmaceutically acceptable excipient.

17. The compound of claim 1 which is 2,2,2-trifluoro-1-(trifluoromethyl)ethyl 4-[(4-chlorobenzenesulphonylamino)methyl]piperidine-1-carboxylate, in the form of the base or of an addition salt with an acid.

18. A pharmaceutical composition comprising a compound according to claim 17 or a pharmaceutically acceptable salt thereof and at least one pharmaceutically acceptable excipient.

19. The compound of claim 1 which is 2,2,2-trifluoro-1-(trifluoromethyl)ethyl 4-[(toluene-2-sulphonylamino)methyl]piperidine-1-carboxylate, in the form of the base or of an addition salt with an acid.

20. A pharmaceutical composition comprising a compound according to claim 19 or a pharmaceutically acceptable salt thereof and at least one pharmaceutically acceptable excipient.

21. The compound of claim 1 which is 2,2,2-trifluoro-1-(trifluoromethyl)ethyl 4-[(3-(trifluoromethyl)benzenesulphonylamino)methyl]piperidine-1-carboxylate, in the form of the base or of an addition salt with an acid.

22. The compound of claim 1 which is 2,2,2-trifluoro-1-(trifluoromethyl)ethyl 4-[(4-methoxybenzenesulphonylamino)methyl]piperidine-1-carboxylate, in the form of the base or of an addition salt with an acid.

23. A pharmaceutical composition comprising a compound according to claim 21 or a pharmaceutically acceptable salt thereof and at least one pharmaceutically acceptable excipient.

24. A pharmaceutical composition comprising a compound according to claim 22 or a pharmaceutically acceptable salt thereof and at least one pharmaceutically acceptable excipient.

25. A compound of formula (I):

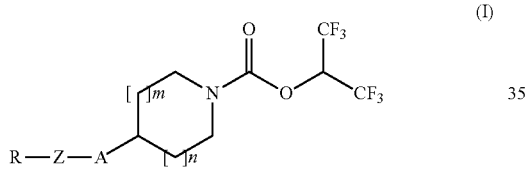

(I)

wherein:
R represents an $R^1$ group substituted by one or more substituents independently selected from the group consisting of $R^2$ and $R^3$;
$R^1$ represents an aryl or heteroaryl group;
$R^2$ represents a halogen atom or a cyano, nitro, oxo, ($C_1$-$C_6$)alkyl, ($C_1$-$C_6$)alkoxy, hydroxyl, ($C_1$-$C_6$)alkylthio, ($C_1$-$C_6$)haloalkyl, ($C_1$-$C_6$)haloalkoxy, ($C_1$-$C_6$)haloalkylthio, $NR^4R^5$, $NR^4COR^5$, $NR^4SO_2R^5$, $COR^4$, $CO_2R^4$, $CONR^4R^5$, $SO_2R^4$, $SO_2NR^4R^5$, or benzyloxy group;
$R^3$ represents a monocyclic aryl or heteroaryl group which can be substituted by one or more $R^2$ groups which are identical to or different from one another;
$R^4$ and $R^5$ represent, independently of one another, a hydrogen atom or a ($C_1$-$C_6$)alkyl group or form, with the nitrogen atom or the N—CO or N—$SO_2$ fragment which carries them, a heterocycle optionally substituted by a ($C_1$-$C_6$)alkyl or benzyl group;
Z represents a bond, a ($C_1$-$C_6$)alkylene group, a ($C_2$-$C_6$)alkenylene group, a ($C_2$-$C_6$)alkynylene group, an O—($C_1$-$C_6$)alkylene group or an $N(R^A)$—($C_1$-$C_6$)alkylene group;
A represents a bond, an oxygen atom, a sulphur atom, an $N(R^A)$ group, an $N(R^A)$—($C_1$-$C_6$)alkylene group, a $CON(R^A)$ group, a $CON(R^A)$—($C_1$-$C_6$)alkylene group, an $SO_2N(R^A)$ group, an $SO_2N(R^A)$—($C_1$-$C_6$)alkylene group, an $OCON(R^A)$ group, an $OCON(R^A)$—($C_1$-$C_6$)alkylene group, an $N(R^B)CON(R^A)$ group, an $N(R^B)CON(R^A)$—($C_1$-$C_6$)alkylene group, an $N(R^B)SO_2N(R^A)$ group, an $N(R^B)SO_2N(R^A)$—($C_1$-$C_6$)alkylene group, an O—($C_1$-$C_6$)alkylene group, an $N(R^B)CO_2$ group, an $N(R^B)CO_2$—($C_1$-$C_6$)alkylene group, an S—($C_1$-$C_6$)alkylene group, an $SO_2$ group, an $SO_2$—($C_1$-$C_6$)alkylene group, an $N(R^B)SO_2$ group, an $N(R^B)SO_2$—($C_1$-$C_6$)alkylene group, a CO group, a CO—($C_1$-$C_6$)alkylene group, an $N(R^B)CO$ group, an $N(R^B)CO$—($C_1$-$C_6$)alkylene group, an $SO_2N(R^B)CO$ group, an $SO_2N(R^B)CO$—($C_1$-$C_6$)alkylene group, an $SO_2N(R^B)CON(R^A)$ group or an $SO_2N(R^B)CON(R^A)$—($C_1$-$C_6$)alkylene group;
$R^A$ and $R^B$ represent, independently of one another, a hydrogen atom or a ($C_1$-$C_6$)alkyl group; and
m and n represent, independently of one another, an integer equal to 0 or 1, in the form of the base or of an addition salt with an acid.

26. A process for the preparation of a compound of formula (I) according to claim 1, comprising reacting a compound of formula (II):

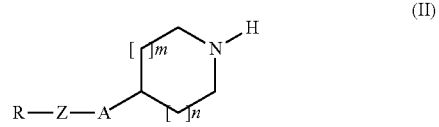

(II)

wherein A, Z, R, m and n are as defined in formula (I) according to claim 1, with a compound of the formula (III):

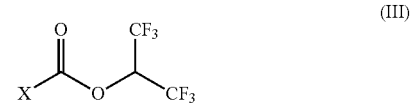

(III)

wherein X represents a leaving group.

27. A process for the preparation of a compound of formula (I) according to claim 1, wherein A represents a $CON(R^A)$, $CON(R^A)$—($C_1$-$C_6$)alkylene, $SO_2N(R^A)$, $SO_2N(R^A)$—($C_1$-$C_6$)alkylene, $N(R^B)CON(R^A)$, $N(R^B)CON(R^A)$—($C_1$-$C_6$) alkylene, $OCON(R^A)$ or $OCON(R^A)$—($C_1$-$C_6$)alkylene group, comprising reacting a compound of formula (IV):

(IV)

wherein R and Z are as defined in formula (I) according to claim 1 and W represents a COCl, $SO_2Cl$, NCO, OCOCl or $N(R^B)COCl$ functional group, $R^A$ and $R^B$ being as defined in the formula (I) of claim 1, with a compound of formula (V):

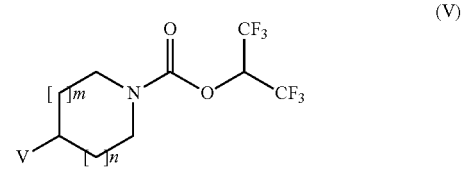

(V)

wherein m and n are as defined in formula (I) according to claim 1 and V represents an amine $HN(R^A)$ or $HN(R^A)$—($C_1$-$C_6$)alkylene functional group.

* * * * *